United States Patent [19]

Hara et al.

[11] Patent Number: 5,792,861
[45] Date of Patent: Aug. 11, 1998

[54] PROCESS FOR THE PRODUCTION OF 4-SUBSTITUTED AZETIDINONE DERIVATIVE

[75] Inventors: Tamio Hara; Yuuki Nakagawa; Nobuo Matsui, all of Toyama-ken; Shigemi Suga, Chiba-ken, all of Japan

[73] Assignees: Tanabe Seiyaku Co., Ltd., Osaka; Nippon Soda Co., Ltd., Tokyo, both of Japan

[21] Appl. No.: 743,327

[22] Filed: Nov. 4, 1996

Related U.S. Application Data

[63] Continuation of Ser. No. 267,358, Jun. 29, 1994, abandoned.

[30] Foreign Application Priority Data

Jun. 30, 1993 [JP] Japan ................................. 5-162604

[51] Int. Cl.$^6$ ................ C07D 205/08; C07D 403/06; C07D 413/06; C07D 417/06
[52] U.S. Cl. .............................................. 540/200
[58] Field of Search ................................. 540/200

[56] References Cited

U.S. PATENT DOCUMENTS

| 5,442,055 | 8/1995 | Iwasaki .................. 540/6 |
| 5,731,431 | 3/1998 | Nakagawa ............... 540/200 |

FOREIGN PATENT DOCUMENTS

| 0197432 | 10/1986 | European Pat. Off. . |
| 597423 | 5/1994 | European Pat. Off. ......... 540/200 |
| 9313064 | 7/1993 | WIPO . |

OTHER PUBLICATIONS

Tetrahedron letters, vol. 27, No. 47, pp. 5687–5690, "Simple and Highly Diastereoselective ... Enolates", Déziel et al. 1986.
Tetrahedron letters, vol. 28, No. 52, pp. 6625–6628, "A Highly Stereoselective Synthesis of a Key ... Derivatives", Ito et al. 1987.
Tetrahedron Letters, vol. 30, No. 41, pp. 5631–5634, "A Novel Synthesis of the 1β-Methycarbapenem ... Derivative", Ito et al. (1989).
Patent Abstracts of Japan, vol. 12, No. 132, "4-Substituted ... Compound", Sugimura MASAO, Apr. 11, 1987, Jap. Pat. No. 62252786.

*Primary Examiner*—Mark L. Berch
*Attorney, Agent, or Firm*—Leydig, Voit & Mayer, Ltd.

[57] ABSTRACT

The present invention provides a process for the production of a 4-substituted azetidinone. The process comprises reacting

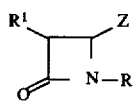

(III)

wherein R represents a hydrogen atom or a protecting group for N, $R^1$ represents an alkyl which may be a substituent having an unprotected or protected hydroxyl group; and Z represents a leaving group; with

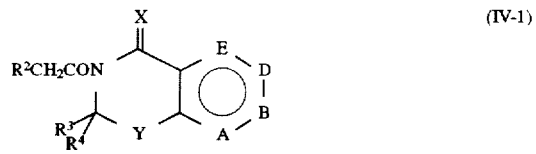

(IV-1)

or

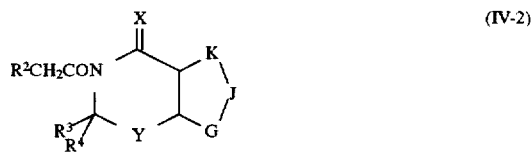

(IV-2)

wherein $R^2$ represents hydrogen or alkyl, $R^3$ and $R^4$ each represent hydrogen, alkyl, alkenyl, alkynyl, phenyl, cycloalkyl, or naphthyl, or $R^3$ and $R^4$, together with the carbon atom to which they are bonded, form a ring system; X and Y each represent oxygen, sulfur or N-$r^1$, wherein $r^1$ represents a hydrogen atom or lower alkyl; A, B, D and E each represent nitrogen or C-$r^2$, wherein $r^2$ represents hydrogen, halogen, lower alkyl or lower alkoxy, provided that at least two of A, B, D and E are C-$r^2$; and a ring involving G, J and K has two carbon/carbon double bonds therein and one of G, J and K represents oxygen, sulfur or N-$r^1$ while the remaining two represent C-$r^2$; in the presence of

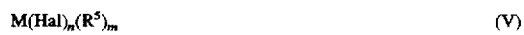

(V)

wherein M represents a metal atom; Hal represents halogen; $R^5$ represents lower alkyl, lower alkoxy, phenoxy, substituted phenoxy or cyclopentadienyl; and n and m are each 0, 1, 2, 3, 4 or 5, provided that n+m stands for the valence of M; and a base to thereby give:

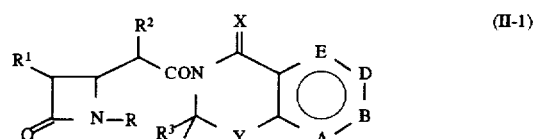

(II-1)

or

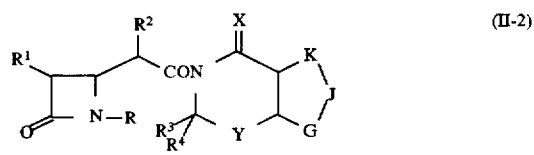

(II-2)

20 Claims, No Drawings

PROCESS FOR THE PRODUCTION OF 4-SUBSTITUTED AZETIDINONE DERIVATIVE

This is a continuation of application Ser. No. 08/267,358 filed on Jun. 29, 1994 abandoned.

BACKGROUND OF THE INVENTION

This invention relates to a process for the production of a 4-substituted azetidinone derivative which is important as an intermediate in the synthesis of carbapenem compounds.

A carboxylic acid derivative represented by the following general formula [I']:

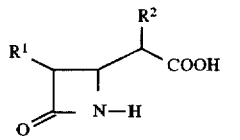

[I']

wherein $R^1$ represents an alkyl group which may be substituted by an optionally protected hydroxyl group or a halogen atom; and $R^2$ represents a hydrogen atom or an alkyl group;

is an important intermediate in the synthesis of carbapenem compounds and there have been proposed several methods for the production thereof.

For example, Japanese Patent Laid-Open No. 252786/1987 has disclosed that a 4-substituted azetidinone represented by the following general formula [II']:

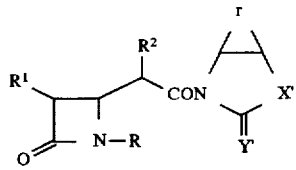

[II']

wherein $R^1$ and $R^2$ are as defined above; R represents a hydrogen atom or a protecting group for N which can be easily eliminated; r represents an optionally substituted aromatic group formed together with the two adjacent carbon atoms; X' represents an oxygen atom, a sulfur atom, SO, $SO_2$ or $Nr^4$, wherein $r^4$ represents a hydrogen atom, an alkyl group or a phenyl group; and Y' represents an oxygen atom, a sulfur atom or $Nr^5$, wherein $r^5$ represents a hydrogen atom, an alkyl group or a phenyl group; is easily hydrolyzed into a carboxylic acid derivative represented by the general formula [I'].

Further, a compound represented by the following general formula [II"]:

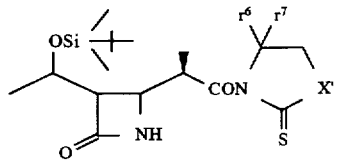

[II"]

wherein X' is as defined above; and $r^6$ and $r^7$ each represent a hydrogen atom or a methyl group; is described in Tetrahedron Lett. Vol. 27, 5687–5690 (1986).

However these 4-substituted azetidinone derivatives represented by the general formulae [II'] and [II"] are produced with the use of highly expensive materials, i.e., boron triflate or tin triflate, which makes them unsuitable for industrial purposes.

SUMMARY OF THE INVENTION

The present invention relates to a process for the production of a 4-substituted azetidinone derivative which com-prises reacting an azetidinone derivative represented by the following general formula:

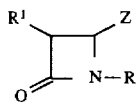

[III]

wherein R represents a hydrogen atom or a protecting group for N which can be easily eliminated, $R^1$ represents an alkyl group which may be substituted by an optionally protected hydroxyl group or a halogen atom; and Z represents a leaving group; with an imide compound represented by the following general formula:

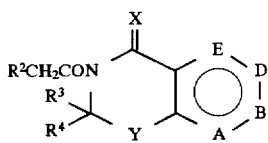

[IV-1]

or

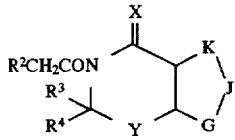

[IV-2]

wherein $R^2$ represents a hydrogen atom or an alkyl group; $R^3$ and $R^4$ each represent a hydrogen atom, an alkyl group, an alkenyl group, an alkynyl group, a phenyl group, a cycloalkyl group, a naphthyl group or a ring formed by $R^3$ together with $R^4$; X and Y each represent an oxygen atom, a sulfur atom or $N-r^1$, wherein $r^1$ represents a hydrogen atom or a lower alkyl group;

A, B, D and E each represent a nitrogen atom or $C-r^2$, wherein $r^2$ represents a hydrogen atom, a halogen atom, a lower alkyl group or a lower alkoxy group, provided that at least two of A, B, D and E are $C-r^2$; and a five-membered ring involving G, J and K has two carbon/carbon double bonds therein and one of G, J and K represents an oxygen atom, a sulfur atom or $N-r^1$ while the remaining two represent $C-r^2$, wherein $r^1$ and $r^2$ are as defined above;

in the presence of a compound represented by the following general formula:

$$M(Hal)_n(R^5)_m \qquad (V)$$

wherein M represents a metal atom; Hal represents a halogen atom; $R^5$ represents a lower alkyl group, a lower alkoxy group, a phenoxy group, a substituted phenoxy group or a cyclopentadienyl group; and n and m are each 0, 1, 2, 3, 4 or 5 provided that n+m stands for the valence of M; and a base to thereby give a 4-substituted azetidinone derivative represented by the following general formulae:

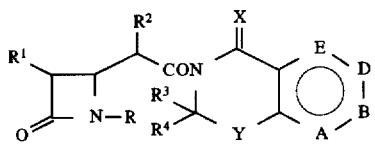

[II-1]

or

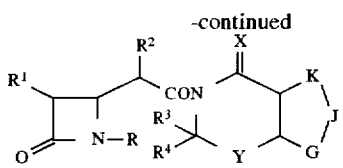

wherein R, $R^1$, $R^2$, $R^3$, $R^4$, X, Y, A, B, D, E, G, J and K are as defined above.

DETAILED DESCRIPTION OF THE PREFERRED EMBODIMENTS

Examples of the protecting group for the hydroxyl group of $R^1$ include organosilyl groups such as tert-butyldimethylsilyl, tert-butyldiphenylsilyl, triethylsilyl, dimethylcumylsilyl, triisopropylsilyl and dimethylhexylsilyl groups, oxycarbonyl groups such as p-nitrobenzyloxycarbonyl, p-methoxybenzyloxy-carbonyl and allyloxycarbonyl groups, acetyl group, triphenylmethyl group, benzoyl group and tetrahydropyranyl group.

Examples of the protecting group for N include the silyl groups as cited above, benzyl group, p-nitrobenzyl group, p-nitrobenzoylmethyl group, benzhydryl group, p-methoxybenzyl group and 2,4-dimethoxybenzyl group.

Examples of the leaving group of Z include acyloxy groups, for example, linear, branched or cyclic alkanoyloxy groups such as acetoxy, propionyloxy, butyryloxy, isobutyryloxy and cyclohexylcarbonyloxy groups, monocyclic or bicyclic aroyloxy groups optionally having a hetero atom such as benzoyloxy, 1-naphthoyloxy, 2-naphthoyloxy, nicotinoyloxy, isonicotinoyloxy, furoyloxy and thenoyloxy groups, arylalkanoyl groups such as phenylacetoxy group, alkylsulfonyloxy groups such as methanesulfonyloxy, ethanesulfonyloxy, propanesulfonyloxy and trifluoromethanesulfonyloxy groups, arylsulfonyloxy groups such as benzenesulfonyloxy and toluenesulfonyloxy groups, alkoxycarbonyloxy groups such as methoxycarbonyloxy and ethoxycarbonyloxy groups, aralkoxycarbonyloxy groups such as benzyloxycarbonyloxy group, alkoxyalkanoyloxy groups such as methoxyacetoxy and ethoxyacetoxy groups, and carbamoyloxy groups such as N-methylcarbamoyloxy, N-ethylcarbamoyloxy and N-phenylcarbamoyloxy groups; acylthio groups, for example, alkanoylthio groups such as acetylthio and propionylthio group and aroylthio groups such as benzoylthio group;

sulfenyl groups, for example, alkylthio groups such as methylthio, ethylthio, propylthio, isopropylthio, butylthio, isobutylthio and tert-butylthio groups and arylthio groups such as phenylthio group; sulfinyl groups, for example, alkylsulfinyl groups such as methanesulfinyl, ethanesulfinyl, propanesulfinyl and butanesulfinyl groups and arylsulfinyl groups such as benzenesulfinyl and toluenesulfinyl groups;

sulfonyl groups, for example, alkylsulfonyl groups such as methanesulfonyl, ethanesulfonyl, propanesulfonyl and butanesulfonyl groups and arylsulfonyl groups such as benzenesulfonyl group; and halogen atoms such as fluorine, chlorine and bromine atoms.

As the above-mentioned base, secondary and tertiary amines and pyridines can be cited. Examples thereof include secondary amines, for example, alkylamines such as dimethylamine, diethylamine, diisopropylamine and dicyclohexylamine, alkylanilines such as N-methylaniline and heterocyclic amines such as piperidine, pyrrolidine, 2,2,6,6-tetramethylpiperidine, morpholine and piperazine, tertiary amines, for example, alkylamines such as diisopropylethylamine, diisopropylmethylamine and triethylamine, dialkylanilines such as N,N-dimethylaniline, heterocyclic amines such as 1-ethylpiperidine, 1-methylmorpholine, 1-ethylpyrrolidine, 1,4-diazabicyclo|2.2.2| octane and 1,8-diazabicyclo|5.4.0|undec-7-ene and diamines such as N,N,N',N'-tetramethylethylenediamine and pyridines, for example alkylpyridines such as α-, β- or γ-picoline, 2,3-, 2,4-, 2,5-, 2,6-, 3,4- or 3,5-lutidine and 2,4,6-collidine, dialkylaminopyridines such as dimethylaminopyridine and condensed heterocyclic pyridines such as quinoline.

Examples of the compound represented by the formula $M(Hal)_n(R^5)_m$ include $TiCl_4$, $TiCl_3(OCH_3)$, $TiCl_3(OC_2H_5)$, $TiCl_3(OC_3H_7{}^n)$, $TiCl_3(OC_3H_7{}^1)$, $TiCl_3(Obu^n)$, $TiCl_3(Obu^1)$, $TiCl_3(Obu^s)$, $TiCl_3(Obu^t)$, $TiCl_2(OCH_3)_2$, $TiCl_2(OC_2H_5)_2$, $TiCl_2(OC_3H_7{}^n)_2$, $TiCl_2(OC_3H_7{}^1)_2$, $TiCl_2(Obu^n)_2$, $ZrCl_4$, $ZrCl_3(OCH_3)$, $ZrCl_3(OC_2H_5)$, $ZrCl_3(OC_3H_7{}^n)$, $ZrCl_3(OC_3H_7{}^1)$ $ZrCl_3(OC_4H_9{}^1)$, $ZrCl_3(OC_4H_9{}^s)$, $ZrCl_3(OC_4H_9{}^t)$, $SnCl_4$, $AlCl_3$, $Al(OCH_3)_3$, $Al(OC_2H_5)_3$, $Al(OC_3H_7{}^1)_3$, $AlCl_2C_2H_5$, $AlCl(C_2H_5)_2$, $Al(C_2H_5)_3$, $AlCl_2CH_3$, $AlCl(CH_3)_2$ and $Al(CH_3)_3$.

Examples of the substituent represented by the following general formulae (hereinafter referred to as the auxiliary group) are as follows:

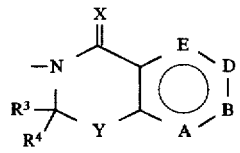

or

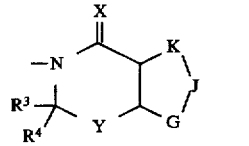

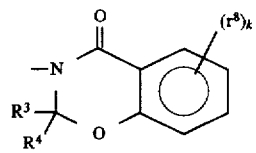

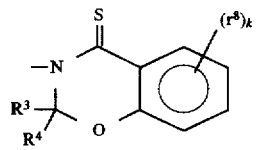

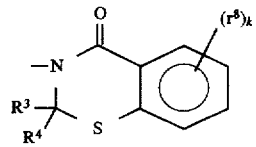

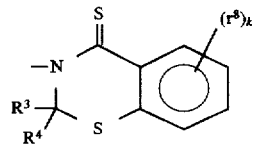

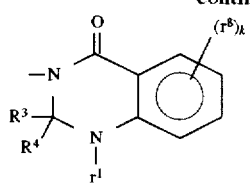
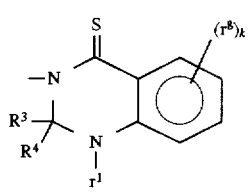
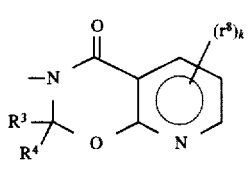
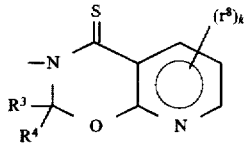
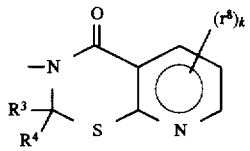
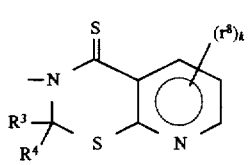
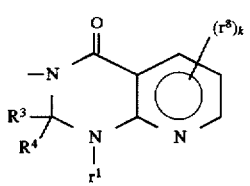
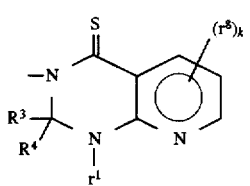
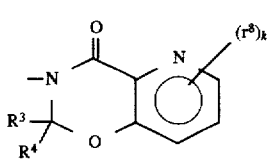
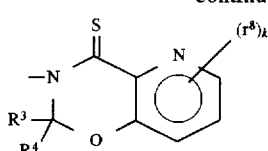
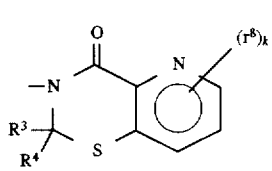
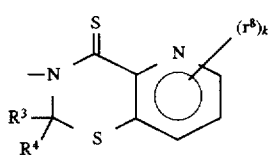
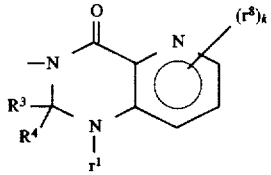
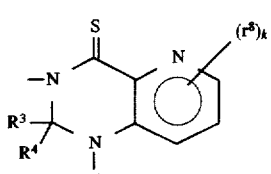
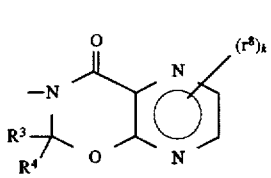
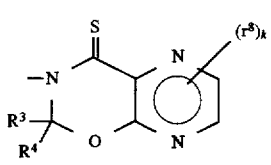
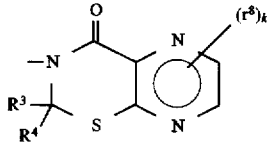
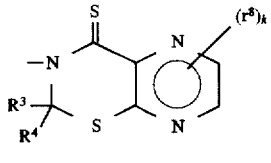

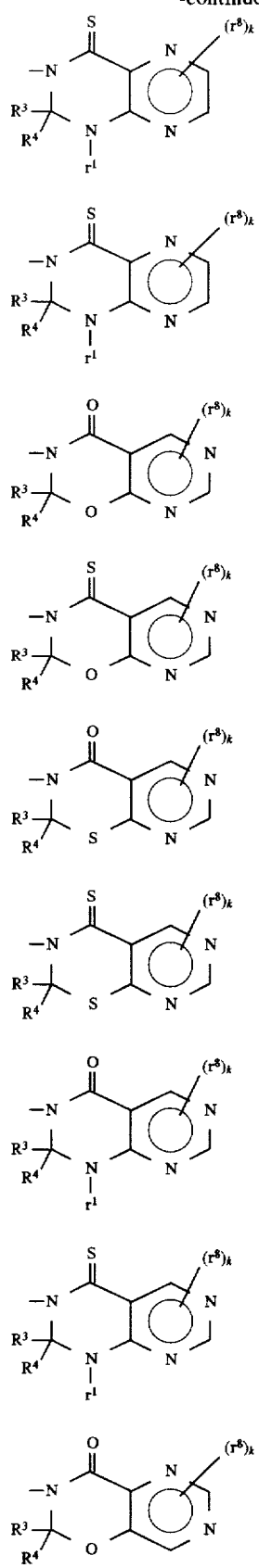
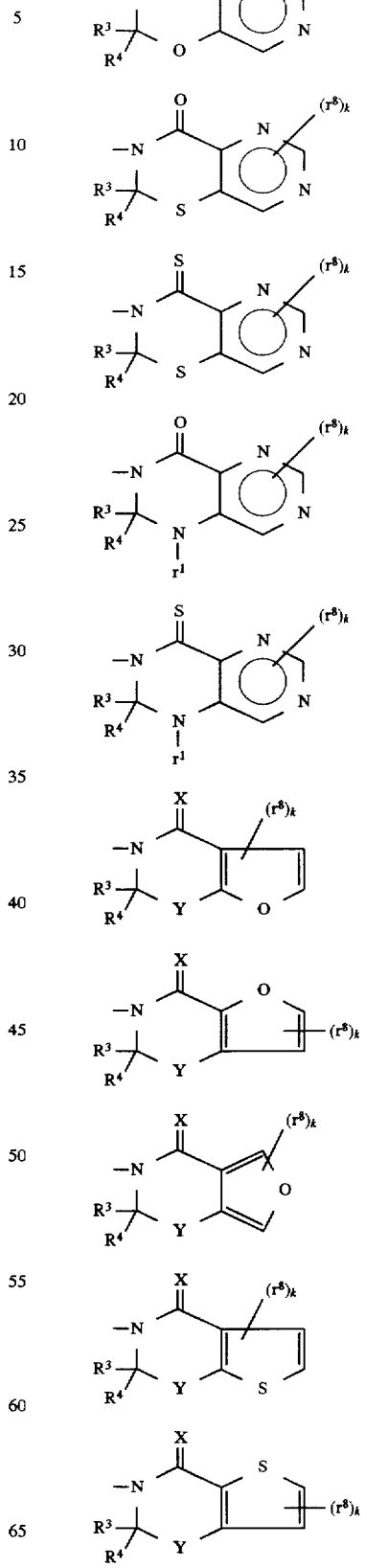

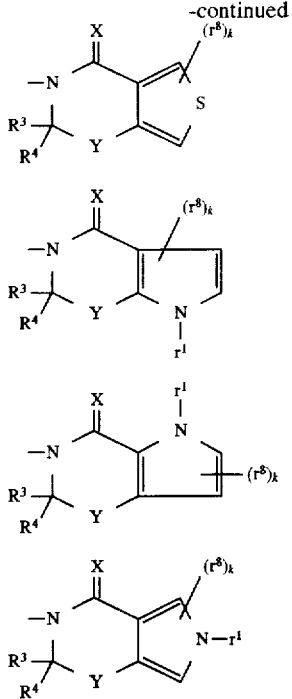

wherein $r^8$ represents a hydrogen atom, a lower alkyl group, a halogen atom or a lower alkoxy group; and k is 0, 1, 2 or 3.

Examples of $R^3$ and $R^4$ in the above formulae include alkyl groups having 1 to 15 carbon atoms such as methyl, ethyl, propyl isopropyl, butyl, isobutyl, s-butyl, t-butyl, pentyl, isopentyl, s-pentyl, neo-pentyl, octyl and decyl groups, alkenyl groups having 2 to 10 carbon atoms such as vinyl, allyl, 1-propenyl and 3-butenyl groups, alkynyl groups having 2 to 10 carbon atoms such as ethynyl and 2-propynyl groups, cycloalkyl groups having 3 to 10 carbon atoms such as cyclopropyl, cyclopentyl and cyclohexyl groups, aralkyl groups having 7 to 10 carbon atoms such as benzyl and phenylethyl groups, aralkenyl groups having 8 to 11 carbon atoms such as a styryl group and aromatic hydrocarbon groups such as phenyl, α-naphthyl and β-naphthyl groups.

Examples of the ring formed by $R^3$ together with $R^4$ are as follows.

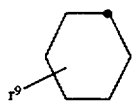

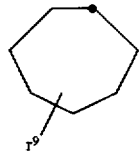

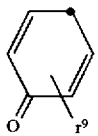

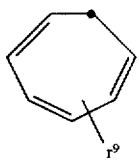

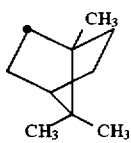

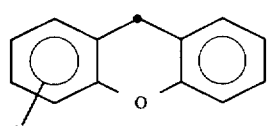

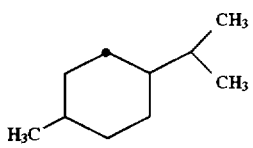

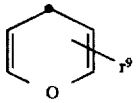

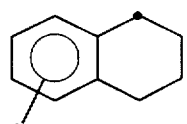

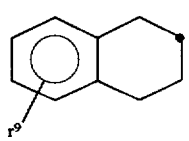

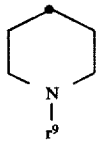

-continued

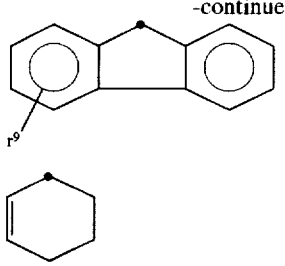

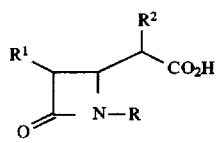

wherein · represents a binding site.

Examples of the substituent $r^9$ include hydrogen atoms, alkyl groups having 1 to 10 carbon atoms, lower alkoxy groups such as methoxy, ethoxy, propoxy, isopropoxy, butoxy, i-butoxy, s-butoxy and t-butoxy groups, phenoxy group, lower alkylthio groups such as methylthio, ethylthio, propylthio and isopropylthio groups, phenylthio group, halogen atoms such as chlorine, bromine and fluorine atoms, oxo group, thioxo group, nitro group, cyano group and substituted amino groups such as dimethylamino, diethylamino and N-methylanilino groups.

The reaction is carried out by forming an enolate from an imide compound represented by the general formula [IV], a compound represented by the general formula [V] and an amine, aniline or pyridine in an organic solvent, for example, a chlorinated solvent such as methylene chloride or chloroform, an aromatic solvent such as chlorobenzene or toluene, a polar solvent such as tetrahydrofuran (THF) or acetonitrile or a mixture thereof and then reacting the enolate thus obtained with an azetidinone derivative represented by the general formula [III]. The formation of the enolate and the reaction between the enolate and the azetidinone derivative are both performed at a reaction temperature of from −50° to 100° C., preferably from −20° to 50° C.

In this reaction, 1 to 8 mol of the imide compound represented by the general formula [IV], 1 to 8 mol of the compound represented by the compound [V] and 1 to 8 mol of the base are each used per mol of the azetidinone derivative represented by the general formula [III].

When $R^2$ is an alkyl group such as a methyl group, the ratio of the α-compound and β-compound thus formed varies depending on the molar ratio of the imide compound represented by the general formula [IV] to the compound represented by the general formula [V] or the amine and the type of the auxiliary group. The yield of the β-compound can be elevated by adding a polar solvent such as DMF, THF or acetonitrile to the reaction system. After the completion of the reaction, the target compound can be isolated by a usual work-up.

The compound [II] obtained by the method of the present invention can be optionally isolated and then hydrolyzed to thereby give a carboxylic acid derivative represented by the general formula [I]:

[I]

$$R^1\underset{O=\underset{N-R}{\diagup}}{\overset{R^2}{\diagdown}}CO_2H$$

wherein R, $R^1$ and $R^5$ are as defined above.

A compound represented by the general formula [IV-1] or [IV-2] can be produced by, for example, reacting a compound represented by the general formula:

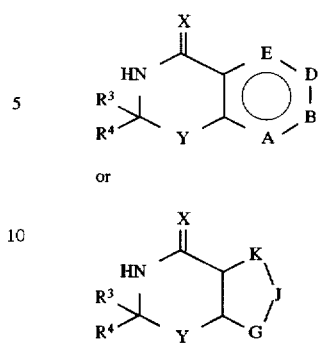

wherein $R^3$, $R^4$, X, Y, A, B, D, E, G, J and K are as defined above;

with a compound represented by the general formula: $R^2CH_2COHal$ wherein $R^2$ is as defined above; and Hal represents a halogen atom;

in an appropriate solvent (for example, toluene, ethyl acetate or methylene chloride) in the presence of a base (for example, triethylamine or pyridine) at a temperature of from −80° C. to the boiling point of the solvent, preferably from −20° to 80° C. Next, an example of the process for the production of the compound represented by the general formula [IV-1] or [IV-2] will be given.

[Production Example 1]

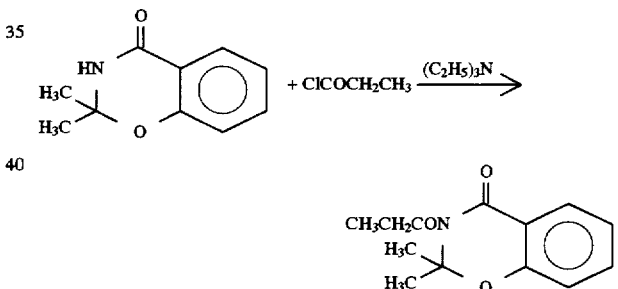

To a mixture of 246.8 g of 2,3-dihydro-2,2-dimethyl-4H-1,3-benzoxazin-4-one and 900 ml of toluene, 142.7 g of propionyl chloride was added. Further, 155.9 g of triethylamine was added dropwise into the mixture at 60° C. After the completion of the reaction, the reaction mixture was cooled and successively washed with water, a dilute aqueous solution of caustic soda and water. After distilling off the solvent, 320 g of the product was obtained.

b.p.: 116° C./2 mmHg.

[Production Example 2]

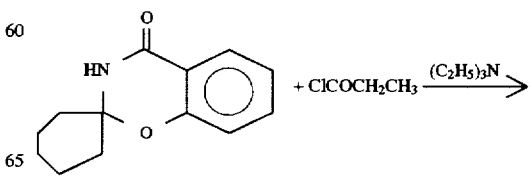

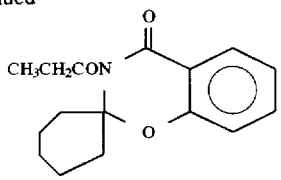

To a mixture of 434.5 g of 2,3-dihydro-2,2-pentamethylene-4H-1,3-benzoxazin-4-one and 4000 ml of toluene, 249.8 g of propionyl chloride was added. Further, 283.3 g of triethylamine was added dropwise into the mixture at 70° C. After the completion of the reaction, the reaction mixture was cooled and successively washed with water, an aqueous solution of sodium hydrogencarbonate and water. After distilling off the solvent and crystallizing from Isopar G (a paraffin solvent), 520 g of the target compound was obtained.

m.p.: 60°–60.5° C.

EXAMPLES

To further illustrate the present invention in greater detail, the following Examples will be given.

Example 1

Production of β-methyl derivative (3-[(R)-2-[(3S,4R)-3-[(R)-1-tert-butyldimethylsilyloxyethyl]-2-oxoazetidin-4-yl)propionyl]-2,3-dihydro-2,2-dimethyl-4H-1,3-benzoxazin-4-one):

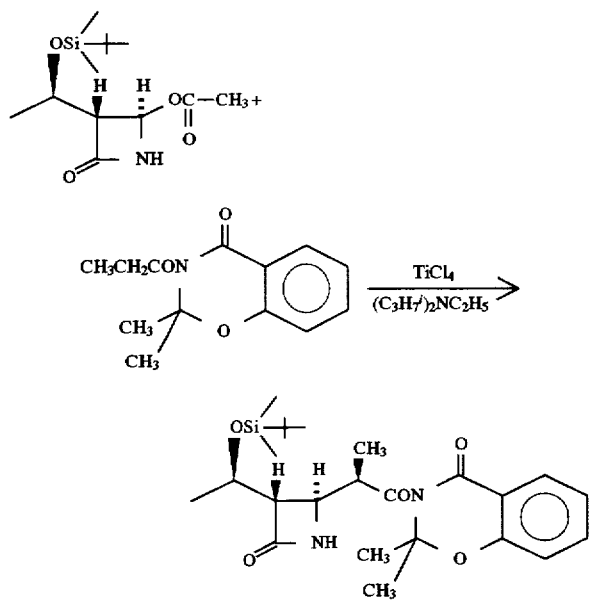

A solution of 2,3-dihydro-2,2-dimethyl-3-propionyl-4H-1,3-benzoxazin-4-one (4.5 g, 19.3 mmol) in methylene chloride (125 ml) was cooled to 5° C. and a solution of titanium tetrachloride (3.7 g, 19.3 mmol) in methylene chloride (5 ml) was added thereto. After aging at 5° C. for 30 minutes, a solution of N,N-diisopropylethylamine (2.5 g, 19.3 mmol) in methylene chloride (5 ml) and a solution of (3R,4R)-4-acetoxy-3-[(R)-1-tert-butyldimethylsilyloxyethyl] azetidin-2-one (2.8 g, 9.7 mmol) in methylene chloride (20 ml) were added thereto at the same temperature. The mixture thus obtained was aged at 5° C. for 1 hour, then heated to 20° C. and aged again for 3 hours. The resulting mixture was added to 300 ml of water at 5° C. under stirring and aged at the same temperature for 30 minutes. The organic layer was separated and analyzed by HPLC. The result showed that it contained 4.1 g of the β-methyl derivative β-methyl derivative:α-methyl derivative=98.6:1.4). The organic layer was washed with 150 ml of water and concentrated under reduced pressure. The residue was purified by silica gel column chromatography to thereby give 3.8 g of the β-methyl derivative (β-methyl derivative : α-methyl derivative=98.2:0.2). The pure β-methyl derivative was obtained by silica gel column chromatography again.

m.p. of β-methyl derivative: 138°–140° C.

Example 2

Production of β-methyl derivative (3-[(R)-2-[(3S,4R)-3-[(R)-1-tert-butyldimethylsilyloxyethyl]-2-oxoazetidin-4-yl)propionyl]-2,2-diethyl-2,3-dihydro-4H-1,3-benzoxazin-4-one):

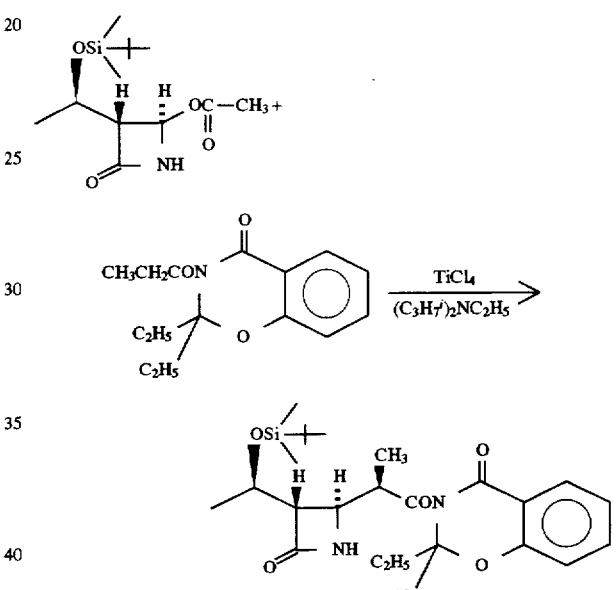

A solution of 2,2-diethyl-2,3-dihydro-3-propionyl-4H-1,3-benzoxazin-4-one (4.1 g, 15.7 mmol) in methylene chloride (45 ml) was cooled to 5° C. and a solution of titanium tetrachloride (3.0 g, 15.7 mmol) in methylene chloride (5 ml) was added thereto. After aging at 5° C. for 30 minutes, a solution of N,N-diisopropylethylamine (2.0 g, 15.7 mmol) in methylene chloride (5 ml) and a solution of (3R,4R)-4-acetoxy-3-[(R)-1-tert-butyldimethylsilyloxyethyl] azetidin-2-one (2.3 g, 7.9 mmol) in methylene chloride (10 ml) were added thereto at the same temperature. The mixture thus obtained was aged at 5° C. for 1 hour, then heated to 20° C. and aged again for 3 hours. The resulting mixture was added to 150 ml of water at 5° C. under stirring and aged at the same temperature for 30 minutes. The organic layer was separated and analyzed by HPLC. The result showed that it contained 3.2 g of the β-methyl derivative β-methyl derivative:α-methyl derivative=94.6:5.4). The organic layer was washed with 150 ml of water and concentrated under reduced pressure. The residue was purified by silica gel column chromatography to thereby give 2.9 g of the β-methyl derivative (β-methyl derivative : α-methyl derivative=95.0:5.0). The pure β-methyl derivative was obtained by purification with silica gel column chromatography again.

m.p. of β-methyl derivative: 184°–185° C.

Example 3

Production of β-methyl derivative (3-[(R)-2-[(3S,4R)-3-[(R)-1-tert-butyldimethylsilyloxyethyl]-2-oxoazetidin-4-yl)propionyl]-2,3-dihydro-2,2-pentamethylene-4H-1,3-benzoxazin-4-one):

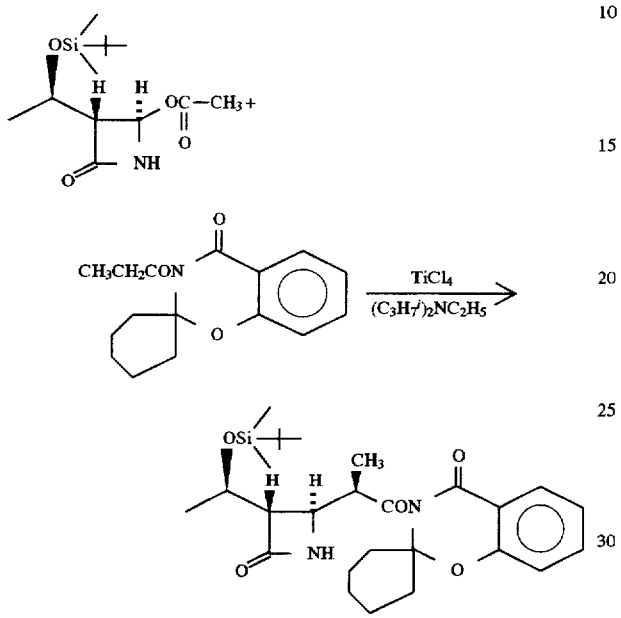

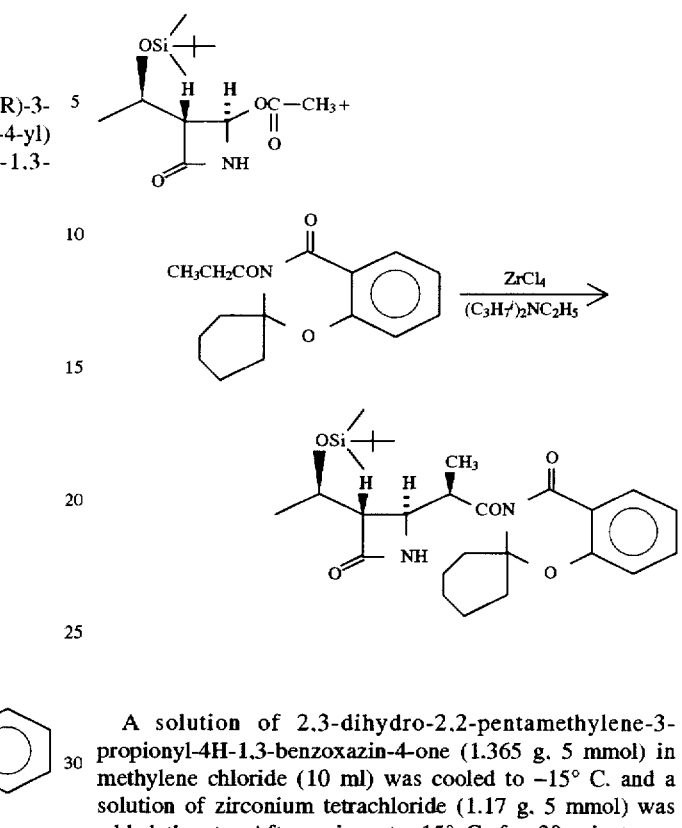

A solution of 2,3-dihydro-2,2-pentamethylene-3-propionyl-4H-1,3-benzoxazin-4-one (5.5 g, 20.1 mmol) in methylene chloride (55 ml) was cooled to 5° C. and a solution of titanium tetrachloride (3.8 g, 20.1 mmol) in methylene chloride (5 ml) was added thereto. After aging at 5° C. for 30 minutes, a solution of N,N-diisopropylethylamine (2.6 g, 20.1 mmol) in methylene chloride (5 ml) and a solution of (3R,4R)-4-acetoxy-3-[(R)-1-tert-butyldimethylsilyloxyethyl] azetidin-2-one (2.9 g, 10.0 mmol) in methylene chloride (10 ml) were added thereto at the same temperature. The mixture thus obtained was aged at 5° C. for 1 hour, then heated to 20° C. and aged again for 3 hours. The resulting mixture was added to 150 ml of water at 5° C. under stirring and aged at the same temperature for 30 minutes. The organic layer was separated and analyzed by HPLC. The result showed that it contained 4.3 g of the β-methyl derivative (β-methylderivative:α-methyl derivative=99.2:0.8). The organic layer was washed with 150 ml of water and concentrated under reduced pressure. The residue was purified by silica gel column chromatography to thereby give 4.0 g of the β-methyl derivative (β-methyl derivative:α-methyl derivative=99.6:0.4). The pure β-methyl derivative was obtained by silica gel column chromatography again.

m.p. of β-methyl derivative: 154°–155° C.

Example 4

Production of β-methyl derivative (3-[(R)-2-[(3S,4R)-3-[(R)-1-tert-butyldimethylsilyloxyethyl]-2-oxoazetidin-4-yl) propionyl]-2,3-dihydro-2,2-pentamethylene-4H-1,3-benzoxazin-4-one):

A solution of 2,3-dihydro-2,2-pentamethylene-3-propionyl-4H-1,3-benzoxazin-4-one (1.365 g, 5 mmol) in methylene chloride (10 ml) was cooled to –15° C. and a solution of zirconium tetrachloride (1.17 g, 5 mmol) was added thereto. After aging at –15° C. for 30 minutes, a solution of N,N-diisopropylethylamine (646 mg, 5 mmol) in methylene chloride (2 ml) and a solution of (3R,4R)-4-acetoxy-3-[(R)-1-tert-butyldimethyl-silyloxy ethyl]-azetidin-2-one (719 mg, 2.5 mmol) in methylene chloride (5 ml) were added thereto at the same temperature. The mixture thus obtained was aged at –15° C. for 1 hour, then heated to 20° C. and aged again for 5 hours. The resulting mixture was cooled to 0° C. and 30 ml of a 10% aqueous solution of sodium hydrogencarbonate was added thereto under stirring. After eliminating the insoluble matter by filtration, the organic layer was separated from the filtrate and analyzed by HPLC. The result showed that it contained 1000 mg of the β-methyl derivative (β-methyl derivative:α-methyl derivative=99:1).

Example 5

Production of β-methyl derivative (3-[(R)-2-[(3S,4R)-3-[(R)-1-tert-butyldimethylsilyloxy-ethyl]-2-oxoazetidin-4-yl)propionyl]-2,3-dihydro-2,2-pentamethylene-4H-1,3-benzoxazin-4-one):

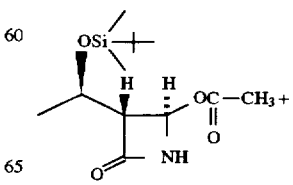

17

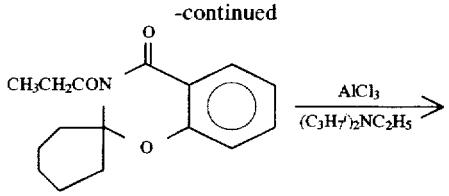

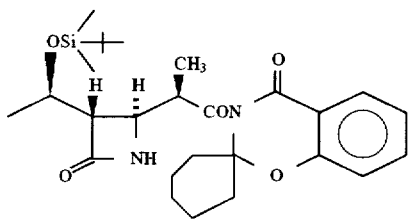

A solution of 2,3-dihydro-2,2-pentamethylene-3-propionyl-4H-1,3-benzoxazin-4-one (1.365 g, 5 mmol) in methylene chloride (10 ml) was cooled to −15° C. and a solution of aluminum chloride (667 mg, 5 mmol) was added thereto. After aging at −15° C. for 30 minutes, a solution of N,N-diisopropylethylamine (646 mg, 5 mmol) in methylene chloride (2 ml) and a solution of (3R,4R)-4-acetoxy-3-[(R)-1-tert-butyldimethylsilyloxyethyl]azetidin-2-one (719 mg, 2.5 mmol) in methylene chloride (5 ml) were added thereto at the same temperature. The mixture thus obtained was aged at −15° C. for 1 hour, then heated to 20° C. and aged again for 5 hours. The resulting mixture was cooled to 0° C. and 30 ml of a 10% aqueous solution of sodium hydrogencarbonate was added thereto under stirring. After eliminating the insoluble matter by filtration, the organic layer was separated from the filtrate and analyzed by HPLC. The result showed that it contained 701 mg of the β-methyl derivative (β-methyl derivative:α-methyl derivative=88:12).

Example 6

Production of β-methyl derivative (3-[(R)-2-[(3S,4R)-3-[(R)-1-tert-butyldimethylsilyloxyethyl]-2-oxoazetidin-4-yl)propionyl]-2,3-dihydro-2,2-pentamethylene-4H-1,3-benzoxazin-4-one):

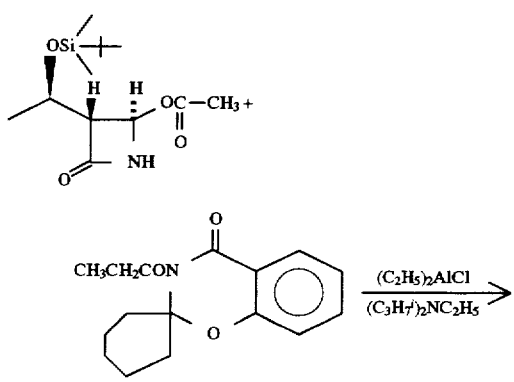

18

A solution of 2,3-dihydro-2,2-pentamethylene-3-propionyl-4H-1,3-benzoxazin-4-one (1.365 g, 5 mmol) in methylene chloride (10 ml) was cooled to −15° C. and a solution of diethylchloro-aluminum/n-hexane (1M, 5 ml, 5 mmol) was added thereto. After aging at −15° C. for 30 minutes, a solution of N,N-diisopropylethylamine (646 mg, 5 mmol) in methylene chloride (2 ml) and a solution of (3R,4R)-4-acetoxy-3-[(R)-1-tert-butyldimethylsilyloxyethyl]azetidin-2-one (719 mg, 2.5 mmol) in methylene chloride (5 ml) were added thereto at the same temperature. The mixture thus obtained was aged at −15° C. for 1 hour, then heated to 20° C. and aged again for 5 hours. The resulting mixture was cooled to 0° C. and 30 ml of a 10% aqueous solution of sodium hydrogencarbonate was added thereto under stirring. After eliminating the insoluble matter by filtration, the organic layer was separated from the filtrate and analyzed by HPLC. The result showed that it contained 190 mg of the β-methyl derivative (β-methyl derivative:α-methyl derivative=52:48).

Example 7

Production of β-methyl derivative (3-[(R)-2-[(3S,4R)-3-[(R)-1-tert-butyldimethylsilyloxyethyl]-2-oxoazetidin-4-yl)propionyl]-2,3-dihydro-2,2-dimethyl-4H-1,3-benzoxazin-4-one):

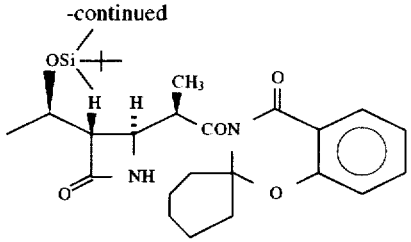

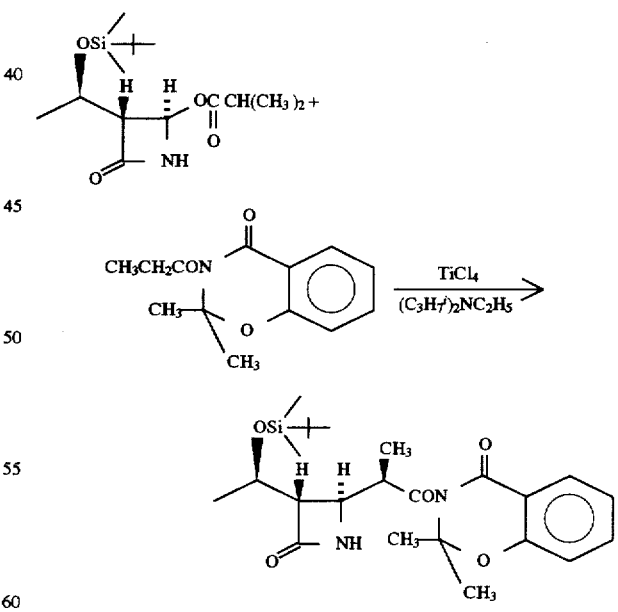

To a solution of 2,3-dihydro-2,2-dimethyl-3-propionyl-4H-1,3-benzoxazin-4-one (3.26 g, 14.0 mmol) in methylene chloride (15 ml), titanium tetrachloride (2.77 g, 14.6 mmol) was added at 5° C. After stirring at the same temperature for 5 minutes, a solution of N,N-diisopropylethylamine (1.74 g, 13.5 mmol) in methylene chloride (10 ml) and a solution of (3R,4R)-3-[(R)-1-tert-butyldimethylsilyloxyethyl]-4-isobutyryloxyazetidin-2-one (3.16 g, 10.0 mmol) in methylene chloride (15 ml) were successively added thereto. The mixture thus obtained was heated to 30° C. and stirred for 2 hours. The reaction mixture was cooled to 0° C. and poured into ice/water under stirring. The organic layer was separated, washed with water and analyzed by HPLC. The result showed that it contained 3.8 g of the β-methyl derivative (β-methyl derivative:α-methyl derivative= 97.7:2.3).

Example 8

Production of β-methyl derivative (3-[(R)-2-[(3S,4R)-3-[(R)-1-tert-butyldimethylsilyloxyethyl]-2-oxoazetidin-4-yl)propionyl]-2,3-dihydro-2,2-dimethyl-4H-1,3-benzoxazin-4-one):

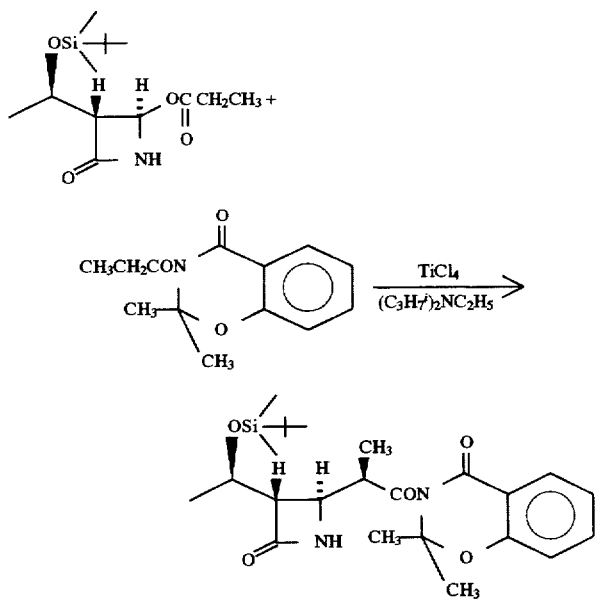

To a solution of 2,3-dihydro-2,2-dimethyl-3-propionyl-4H-1,3-benzoxazin-4-one (3.26 g, 14.0 mmol) in methylene chloride (15 ml), titanium tetrachloride (2.75 g, 14.5 mmol) was added at 5° C. After stirring at the same temperature for 5 minutes, a solution of N,N-diisopropylethylamine (1.75 g, 13.5 mmol) in methylene chloride (10 ml) and a solution of (3R,4R)-3-[(R)-1-tert-butyldimethylsilyloxyethyl]-4-propionyloxyazetidin-2-one (3.02 g, 10.0 mmol) in methylene chloride (15 ml) were successively added thereto. The mixture thus obtained was heated to 30° C. and stirred for 2 hours. The reaction mixture was cooled to 0° C. and poured into ice/water under stirring. The organic layer was separated, washed with water and analyzed by HPLC. The result showed that it contained 4.0 g of the β-methyl derivative (β-methyl derivative:α-methyl derivative= 98.4:1.6).

Example 9

Production of β-methyl derivative (3-[(R)-2-[(3S,4R)-3-[(R)-1-tert-butyldimethylsilyloxyethyl]-2-oxoazetidin-4-yl)propionyl]-2,3-dihydro-2,2-dimethyl-4H-1,3-benzoxazin-4-one):

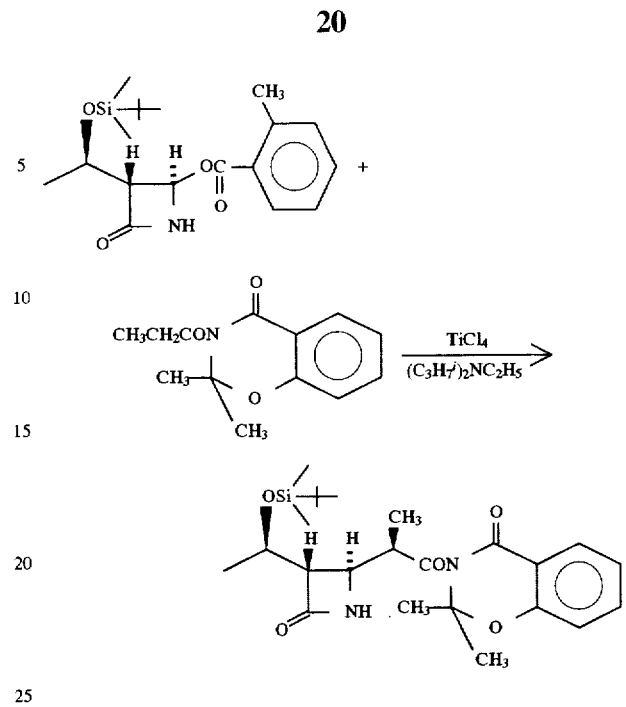

To a solution of 2,3-dihydro-2,2-dimethyl-3-propionyl-4H-1,3-benzoxazin-4-one (3.27 g, 14.0 mmol) in methylene chloride (15 ml), titanium tetrachloride (2.76 g, 14.5 mmol) was added at 5° C. After stirring at the same temperature for 5 minutes, a solution of N,N-diisopropylethylamine (1.74 g, 13.4 mmol) in methylene chloride (10 ml) and a solution of (3R,4R)-3-[(R)-1-tert-butyldimethylsilyloxyethyl]-4-[2-methylbenzoyloxy]azetidin-2-one (3.64 g, 10.0 mmol) in methylene chloride (15 ml) were successively added thereto. The mixture thus obtained was heated to 30° C. and stirred for 2 hours. The reaction mixture was cooled to 0° C. and poured into ice/water under stirring. The organic layer was separated, washed with water and analyzed by HPLC. The result showed that it contained 4.1 g of the β-methyl derivative (β-methyl derivative:α-methyl derivative 97.8:2.2).

Example 10

Production of β-methyl derivative (3-[(R)-2-[(3S,4R)-3-[(R)-1-tert-butyldimethylsilyloxyethyl]-2-oxoazetidin-4-yl)propionyl]-2,3-dihydro-2,2-dimethyl-4H-1,3-benzoxazin-4-one):

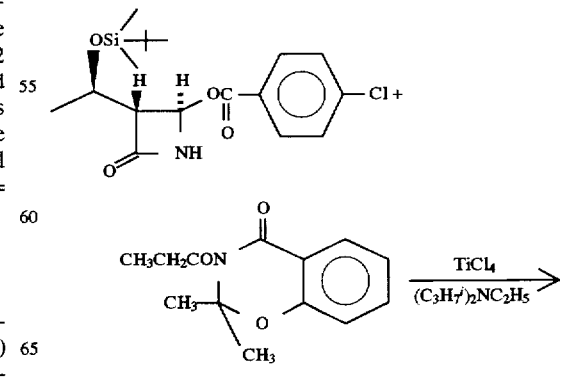

21

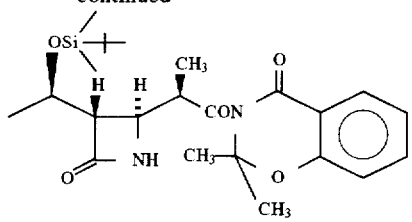

To a solution of 2,3-dihydro-2,2-dimethyl-3-propionyl-4H-1,3-benzoxazin-4-one (3.27 g, 14.0 mmol) in methylene chloride (15 ml), titanium tetrachloride (2.79 g, 14.7 mmol) was added at 5° C. After stirring at the same temperature for 5 minutes, a solution of N,N-diisopropylethylamine (1.74 g, 13.5 mmol) in methylene chloride (10 ml) and a solution of (3R,4R)-3-[(R)-1-tert-butyldimethylsilyloxyethyl]-4-[4-chlorobenzoyloxylazetidin-2-one (3.84 g, 10.0 mmol) in methylene chloride (15 ml) were successively added thereto. The mixture thus obtained was heated to 30° C. and stirred for 2 hours. The reaction mixture was cooled to 0° C. and poured into ice/water under stirring. The organic layer was separated, washed with water and analyzed by HPLC. The result showed that it contained 4.2 g of the β-methyl derivative (β-methyl derivative:α-methyl derivative=98.3:1.7).

Example 11

Production of β-methyl derivative (3-[(R)-2-[(3S,4R)-3-[(R)-1-tert-butyldimethylsilyloxyethyl]-2-oxoazetidin-4-yl)propionyl]-2,3-dihydro-2,2-dimethyl-4H-1,3-benzoxazin-4-one):

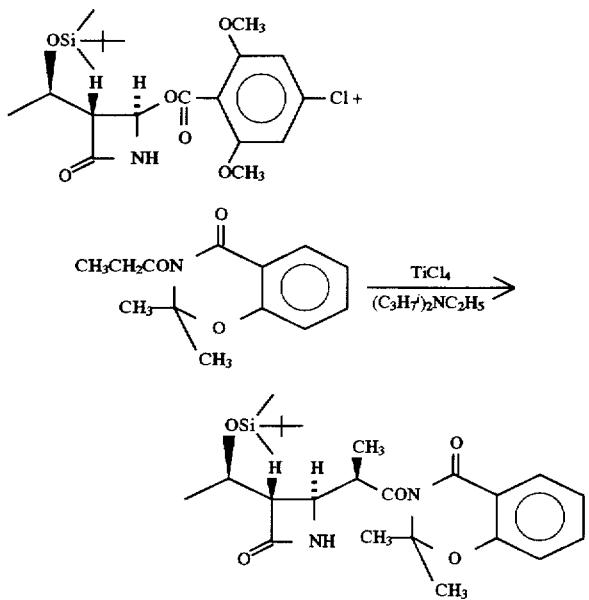

To a solution of 2,3-dihydro-2,2-dimethyl-3-propionyl-4H-1,3-benzoxazin-4-one (16.33 g, 70.0 mmol) in methylene chloride (100 ml), titanium tetrachloride (13.70 g, 72.2 mmol) was added at 5° C. After stirring at the same temperature for 5 minutes, a solution of N,N-diisopropylethylamine (8.72 g, 67.5 mmol) in methylene chloride (50 ml) and a solution of (3R,4R)-3-[(R)-1-tert-butyldimethylsilyloxyethyl]-4-[2,6-dimethoxybenzoyloxy]-azetidin-2-one (20.49 g, 50.0 mmol) in methylene chloride

22

(50 ml) were successively added thereto. The mixture thus obtained was heated to 30° C. and stirred for 2 hours. The reaction mixture was cooled to 0° C. and poured into ice/water under stirring. The organic layer was separated, washed with water and analyzed by HPLC. The result showed that it contained 20.0 g of the β-methyl derivative (β-methyl derivative:α-methyl derivative=97.1:2.9).

Example 12

Production of β-methyl derivative (3-[(R)-2-[(3S,4R)-3-[(R)-1-tert-butyldimethylsilyloxyethyl]-2-oxoazetidin-4-yl)propionyl]-2,3-dihydro-2,2-dimethyl-4H-1,3-benzoxazin-4-one):

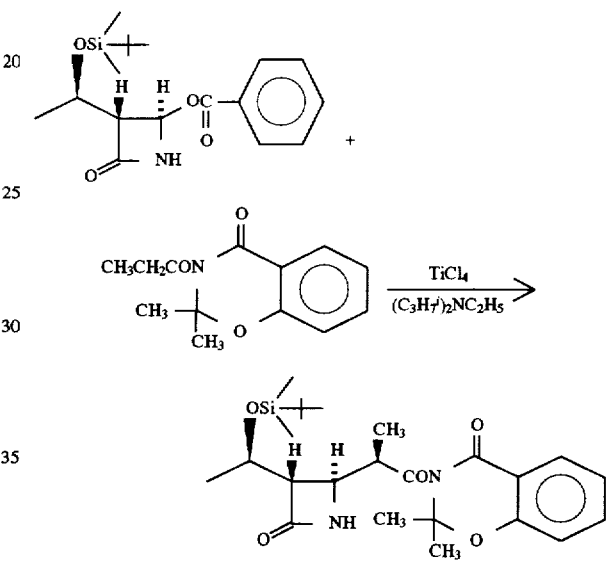

To a solution of 2,3-dihydro-2,2-dimethyl-3-propionyl-4H-1,3-benzoxazin-4-one (16.33 g, 70.0 mmol) in methylene chloride (100 ml), titanium tetrachloride (13.75 g, 72.5 mmol) was added at 5° C. After stirring at the same temperature for 5 minutes, a solution of N,N-diisopropylethylamine (8.73 g, 67.5 mmol) in methylene chloride (50 ml) and a solution of (3R,4R)-4-benzoyloxy-3-[(R)-1-tert-butyldimethyl-silyloxyethyl]azetidin-2-one (17.47 g, 50.0 mmol) in methylene chloride (50 ml) were successively added thereto. The mixture thus obtained was heated to 30° C. and stirred for 2 hours. The reaction mixture was cooled to 0° C. and poured into ice/water under stirring. The organic layer was separated, washed with water and analyzed by HPLC. The result showed that it contained 20.5 g of the β-methyl derivative (β-methyl derivative:α-methyl derivative=98.4:1.6).

Example 13

Production of β-methyl derivative (3-[(R)-2-[(3S,4R)-3-[(R)-1-tert-butyldimethylsilyloxyethyl]-2-oxoazetidin-4-yl)propionyl]-2,3-dihydro-2,2-dimethyl-4H-1,3-benzoxazin-4-one):

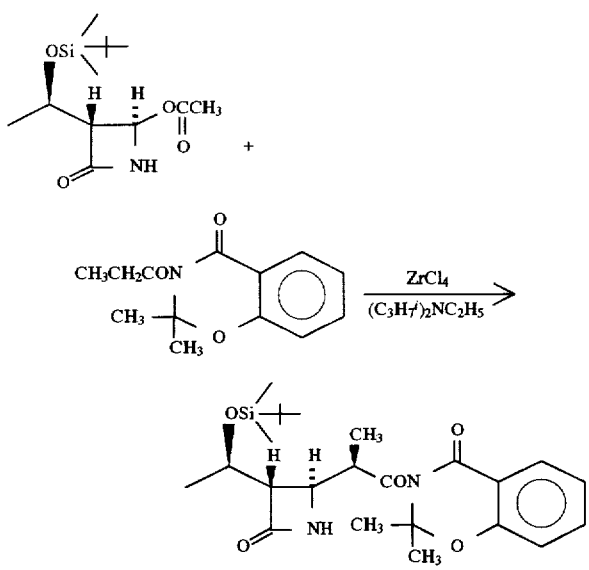

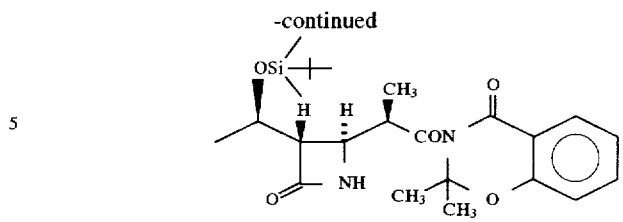

A solution of 2,3-dihydro-2,2-dimethyl-3-propionyl-4H-1,3-benzoxazin-4-one (1.365 g, 5 mmol) in methylene chloride (10 ml) was cooled to −15° C. and zirconium tetrachloride (1.17 g, 5 mmol) was added thereto. After aging at −15° C. for 30 minutes, a solution of N,N-diisopropylethylamine (640 mg, 5 mmol) in methylene chloride (2 ml) and a solution of (3R,4R)-4-acetoxy-3-[(R)-1-tert-butyldimethylsilyloxyethyl]azetidin-2-one (719 mg, 2.5 mmol) in methylene chloride (5 ml) were successively added thereto at the same temperature. The mixture thus obtained was aged at −15° C. for 1 hour, heated to 20° C. and then aged again for 5 hours. The mixture thus obtained was cooled to 0° C. and 30 ml of a 10% aqueous solution of sodium hydrogencarbonate was added thereto under stirring. After eliminating the insoluble matters by filtration, the organic layer was separated from the filtrate and analyzed by HPLC. The result showed that it contained 920 mg of the β-methyl derivative β-methyl derivative:α-methyl derivative=99:1).

Example 14

Production of β-methyl derivative (3-[(R)-2-[(3S,4R)-3-[(R)-1-tert-butyldimethyl-silyloxyethyl]-2-oxoazetidin-4-yl)propionyl]-2,3-dihydro-2,2-dimethyl-4H-1,3-benzoxazin-4-one):

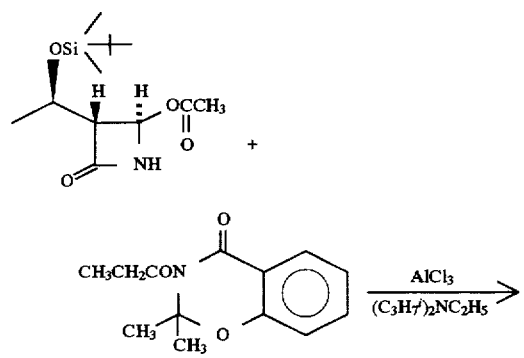

A solution of 2,3-dihydro-2,2-dimethyl-3-propionyl-4H-1,3-benzoxazin-4-one (1.365 g, 5 mmol) in methylene chloride (10 ml) was cooled to −15° C. and aluminum chloride (667 mg, 5 mmol) was added thereto. After aging at −15° C. for 30 minutes, a solution of N,N-diisopropylethylamine (640 mg, 5 mmol) in methylene chloride (2 ml) and a solution of (3R,4R)-4-acetoxy-3-[(R)-1-tert-butyldimethylsilyloxyethyl] azetidin-2-one (719 mg, 2.5 mmol) in methylene chloride (5 ml) were successively added thereto at the same temperature. The mixture thus obtained was aged at −15° C. for 1 hour, heated to 20° C. and then aged again for 5 hours. The mixture thus obtained was cooled to 0° C. and 30 ml of a 10% aqueous solution of sodium hydrogencarbonate was added thereto under stirring. After eliminating the insoluble by filtration, the organic layer was separated from the filtrate and analyzed by HPLC. The result showed that it contained 630 mg of the β-methyl derivative β-methyl derivative:α-methyl derivative=85:15).

Example 15

Production of β-methyl derivative (3-[(R)-2-[(3S,4R) -3-[(R)-1-tert-butyldimethylsilyloxyethyl]-2-oxoazetidin-4-yl) propionyl]-2,3-dihydro-2-isobutyl-2-methyl-4H-1,3-benzoxazin-4-one):

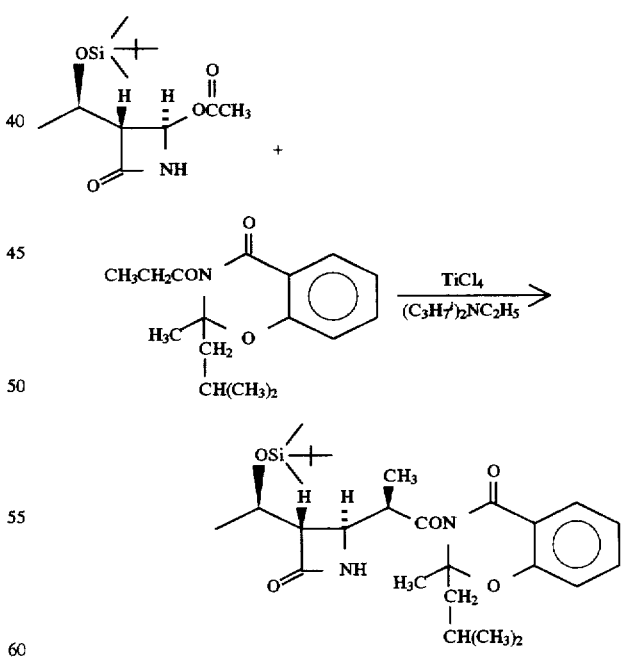

A solution of (±) 2,3-dihydro-2-isobutyl-2-methyl-3-propionyl-4H-1,3-benzoxazin-4-one (9.0 g, 32.7 mmol) in methylene chloride (100 ml) was cooled to 5° C. and a solution of titanium tetrachloride (6.2 g, 32.7 mmol) in methylene chloride (5 ml) was added thereto. After aging at 5° C. for 30 minutes, a solution of N,N- diisopropylethylamine (4.2 g, 32.7 mmol) in methylene chloride (5 ml) and a solution of (3R,4R)-4-acetoxy-3-[(R)-1-tert-butyldimethylsilyloxyethyl]azetidin-2-one (4.7 g, 16.4 mmol) in methylene chloride (20 ml) were successively added thereto at the same temperature. The mixture thus obtained was aged at 5° C. for 1 hour, heated to 20° C. and then aged again for 3 hours. The mixture thus obtained was added to 250 ml of water at 5° C. under stirring and aged at the same temperature for 30 minutes. Then the organic layer was separated and analyzed by HPLC. The result showed that it contained 7.3 g of the β-methyl derivative. The organic layer was washed with 250 ml of water and concentrated under reduced pressure. The residue was purified by silica gel column chromatography to thereby give 6.5 g of the β-methyl derivative (m.ps. of two diastereoisomers: 123°–124° C., 134°–135° C.).

Example 16

Production of β-methyl derivative (3-[(R)-2-[(3S,4R)-3-[(R)-1-tert-butyldimethylsilyloxyethyl]-2-oxoazetidin-4-yl)propionyl]-2,3-dihydro-2-ethyl-2-isopropyl-4H-1,3-benzoxazin-4-one):

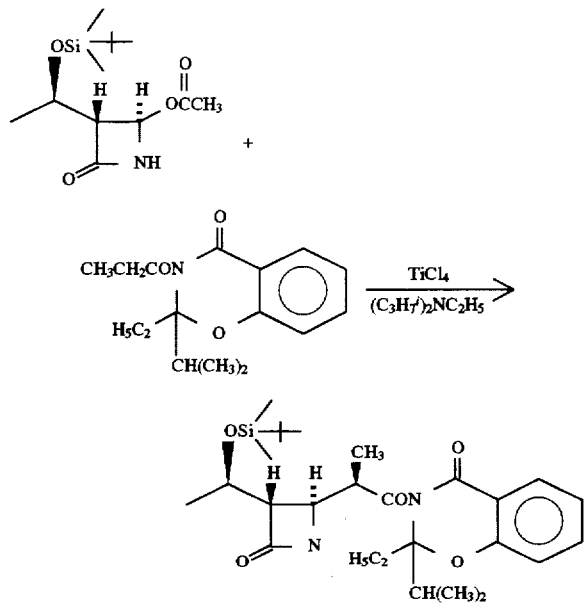

A solution of (±) 2-ethyl-2,3-dihydro-2-isopropyl-3-propionyl-4H-1,3-benzoxazin-4-one (2.8 g, 10 mmol) in methylene chloride (20 ml) was cooled to 5° C. and a solution of titanium tetrachloride (1.9 g, 10 mmol) in methylene chloride (5 ml) was added thereto. After aging at 5° C. for 30 minutes, a solution of N,N-diisopropylethylamine (1.3 g, 10 mmol) in methylene chloride (5 ml) and a solution of (3R,4R)-4-acetoxy-3-[(R)-1-tert-butyldimethylsilyloxyethyl] azetidin-2-one (1.4 g, 5 mmol) in methylene chloride (10 ml) were successively added thereto at the same temperature. The mixture thus obtained was aged at 5° C. for 1 hour, heated to 20° C. and then aged again for 3 hours. The mixture thus obtained was added to 75 ml of water at 5° C. under stirring and aged at the same temperature for 30 minutes. Then the organic layer was separated and analyzed by HPLC. As a result, it contained 1.5 g of the β-methyl derivative. The organic layer was washed with 75 ml of water and concentrated under reduced pressure. The residue was purified by silica gel column chromatography to thereby give 1.4 g of the β-methyl derivative. Based on a chart of ¹H NMR (270Mhz, CDCl₃), it was found out that the derivative thus obtained was a mixture of two diastereoisomers.

Example 17

Production of β-methyl derivative (3-[(R)-2-[(3S,4R)-3-[(R)-1-tert-butyldimethylsilyloxyethyl]-2-oxoazetidin-4-yl)propionyl]-2,3-dihydro-2,2-hexamethylene-4H-1,3-benzoxazin-4-one):

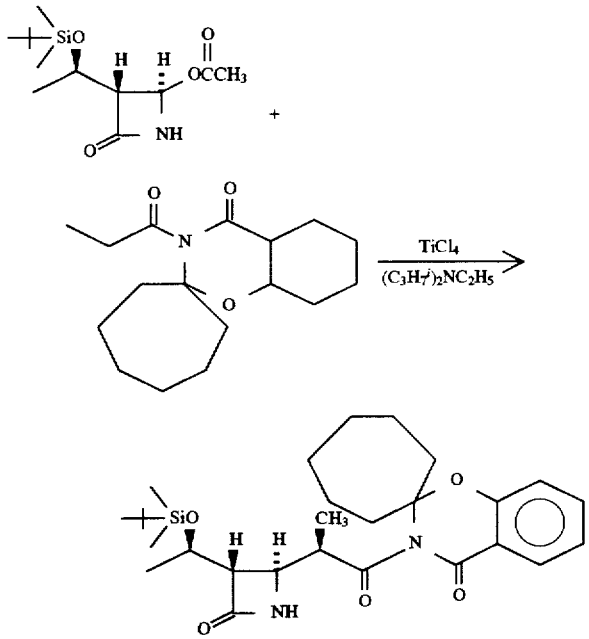

A solution of 2,3-dihydro-2,2-hexamethylene-3-propionyl-4H-1,3-benzoxazin-4-one (5.8 g, 20.3 mmol) in methylene chloride (50 ml) was cooled to 5° C. and a solution of titanium tetrachloride (3.9 g, 20.3 mmol) in methylene chloride (5 ml) was added thereto. After aging at 5° C. for 30 minutes, a solution of N,N-diisopropylethylamine (2.6 g, 20.3 mmol) in methylene chloride (5 ml) and a solution of (3R,4R)-4-acetoxy-3-[(R)-1-tert-butyldimethylsilyloxyethyl] azetidin-2-one (2.9 g, 10.0 mmol) in methylene chloride (10 ml) were successively added thereto at the same temperature. The mixture thus obtained was aged at 5° C. for 1 hour, heated to 20° C. and then aged again for 3 hours. The mixture thus obtained was added to 150 ml of water at 5° C. under stirring and aged at the same temperature for 30 minutes. Then the organic layer was separated and analyzed by HPLC. The result showed that it contained 2.5 g of the β-methyl derivative (β-methyl derivative:α-methyl derivative=98.8:1.2). The organic layer was washed with 150 ml of water and concentrated under reduced pressure. The residue was purified by silica gel column chromatography to thereby give 2.5 g of the β-methyl derivative. (β-methyl derivative:α-methyl derivative=97.9:2.1). The pure β-methyl derivative was obtained by silica gel column chromatography again.

m.p. of β-methyl derivative: 154°–155° C.

Example 18

Production of β-methyl derivative (3-[(R)-2-[(3S,4R)-3-[(R)-1-tert-butyldimethylsilyloxyethyl]-2-oxoazetidin-4-yl)propionyl]-2,3-dihydro-2,2-tetramethylene-4H-1,3-benzoxazin-4-one):

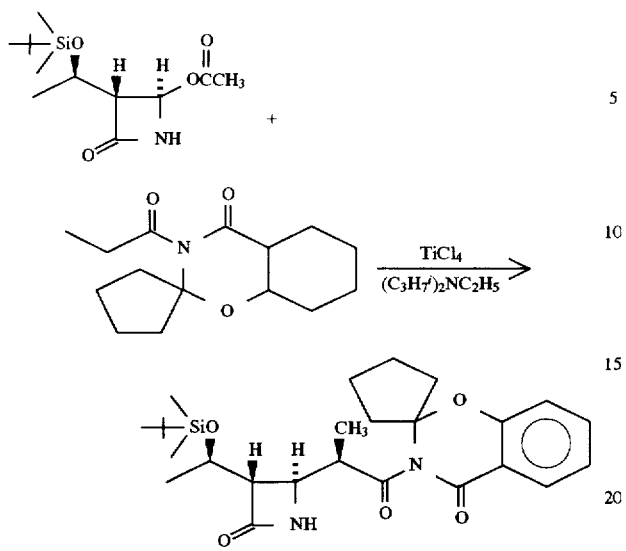

A solution of 2,3-dihydro-2,2-tetramethylene-3-propionyl-4H-1,3-benzoxazin-4-one (2.6 g, 10 mmol) in methylene chloride (20 ml) was cooled to 5° C. and a solution of titanium tetrachloride (1.9 g, 10 mmol) in methylene chloride (5 ml) was added thereto. After aging at 5° C. for 30 minutes, a solution of N,N-diisopropylethylamine (1.3 g, 10 mmol) in methylene chloride (5 ml) and a solution of (3R,4R)-4-acetoxy-3-[(R)-1-tert-butyldimethylsilyloxyethyl] azetidin-2-one (1.4 g, 5 mmol) in methylene chloride (10 ml) were successively added thereto at the same temperature. The mixture thus obtained was aged at 5° C. for 1 hour, heated to 20° C. and then aged again for 3 hours. The mixture thus obtained was added to 75 ml of water at 5° C. under stirring and aged at the same temperature for 30 minutes. Then the organic layer was separated and analyzed by HPLC. The result showed that it contained 2.1 g of the β-methyl derivative (β-methyl derivative:α-methyl derivative=99.2:0.8). The organic layer was washed with 75 ml of water and concentrated under reduced pressure. The residue was purified by silica gel column chromatography to thereby give 2.1 g of the β-methyl derivative. (β-methyl derivative:α-methyl derivative=99.1:0.9). The pure β-methyl derivative was obtained by silica gel column chromatography again.

$^1$H NMR (270 Mhz, CDCl$_3$)δ of β-methyl derivative: 0.01(6H,s), 0.78(9H,s), 1.15(3H,d), 1.20(3H,d), 1.74–2.17 (8H,m), 3.14–3.16(1H,m), 3.55–3.57(1H,m), 3.93–3.95(1H, m), 4.11–4.15(1H,m), 6.09(1H,s), 6.86(1H,dd), 7.03(1H,m), 7.44(1H,m), 7.86(1H,dd).

Example 19

Production of β-methyl derivative (3-[(R)-2-[(3S,4R)-3-[(R)-1-tert-butyldimethylsilyloxyethyl]-2-oxoazetidin-4-yl) propionyl]-2,3-dihydro-2,2-pentamethylene-4H-1,3-benzoxazin-4-one):

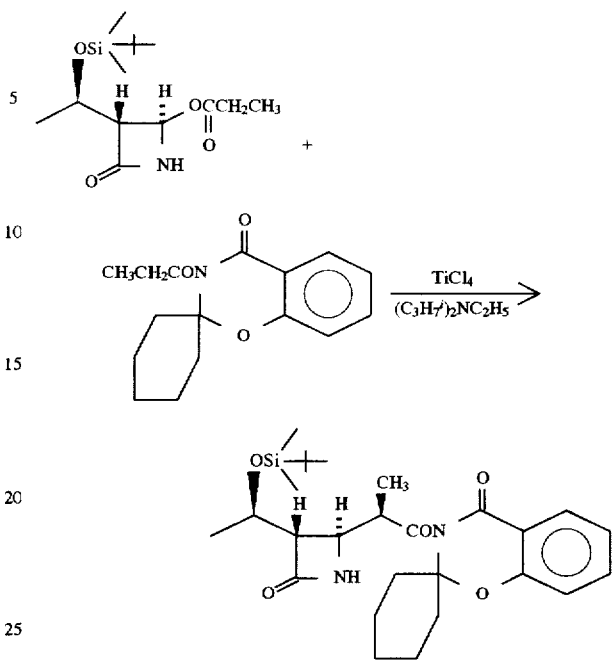

To a solution of 2,3-dihydro-2,2-pentamethylene-3-propionyl-4H-1,3-benzoxazin-4-one (3.82 g, 14.0 mmol) in methylene chloride (15 ml), titanium tetrachloride (2.75 g, 14.5 mmol) was added at 5° C. After stirring at the same temperature for 5 minutes, a solution of N,N-diisopropylethylamine (1.75 g, 13.5 mmol) in methylene chloride (10 ml) and a solution of (3R,4R)-3-[(R)-1-tert-butyldimethylsilyloxyethyl]-4-propionyloxyazetidin-2-one (3.04 g, 10.1 mmol) in methylene chloride (15 ml) were successively added thereto. Then the mixture thus obtained was heated to 30° C. and stirred for 3 hours. The mixture was cooled to 0° C. and poured into ice/water under stirring. Then the organic layer was separated, washed with water and analyzed by HPLC. As a result, it contained 4.1 g of the β-methyl derivative (β-methyl derivative:α-methyl derivative=98.7:1.3).

Example 20

Production of β-methyl derivative (3-[(R)-2-[(3S,4R)-3-[(R)-1-tert-butyldimethylsilyloxyethyl]-2-oxoazetidin-4-yl) propionyl]-2,3-dihydro-2,2-pentamethylene-4H-1,3-benzoxazin-4-one):

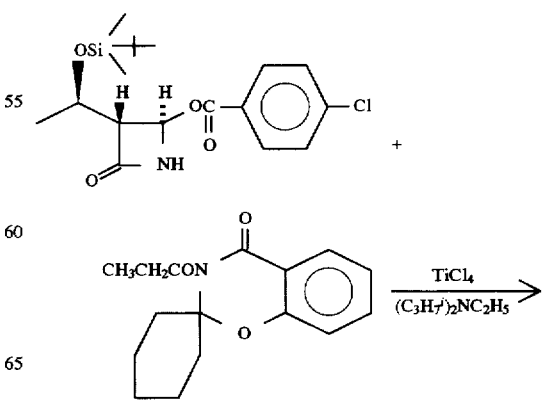

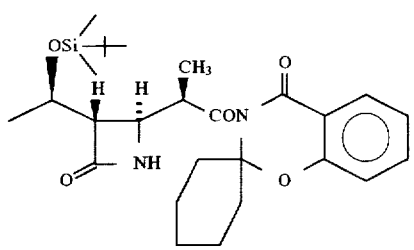

To a solution of 2,3-dihydro-2,2-pentamethylene-3-propionyl-4H-1,3-benzoxazin-4-one (3.82 g, 14.0 mmol) in methylene chloride (15 ml), titanium tetrachloride (2.77 g, 14.6 mmol) was added at 5° C. After stirring at the same temperature for 5 minutes, a solution of N,N-diisopropylethylamine (1.74 g, 13.5 mmol) in methylene chloride (10 ml) and a solution of (3R,4R)-3-[(R)-1-tert-butyldimethylsilyloxyethyl]-4-[4-chlorobenzoyloxy] azetidin-2-one (3.84 g, 10.0 mmol) in methylene chloride (15 ml) were successively added thereto. Then the mixture thus obtained was heated to 30° C. and stirred for 2.5 hours. The mixture was cooled to 0° C. and poured into ice/water under stirring. Then the organic layer was separated, washed with water and analyzed by HPLC. The result showed that it contained 4.4 g of the β-methyl derivative (β-methyl derivative:α-methyl derivative=98.2:1.8).

Example 21

Production of β-methyl derivative (3-[(R)-2-[(3S,4R)-3-[(R)-1-tert-butyldimethylsilyloxyethyl]-2-oxoazetidin-4-yl) propionyl]-2,3-dihydro-2,2-pentamethylene-4H-1,3-benzoxazin-4-one):

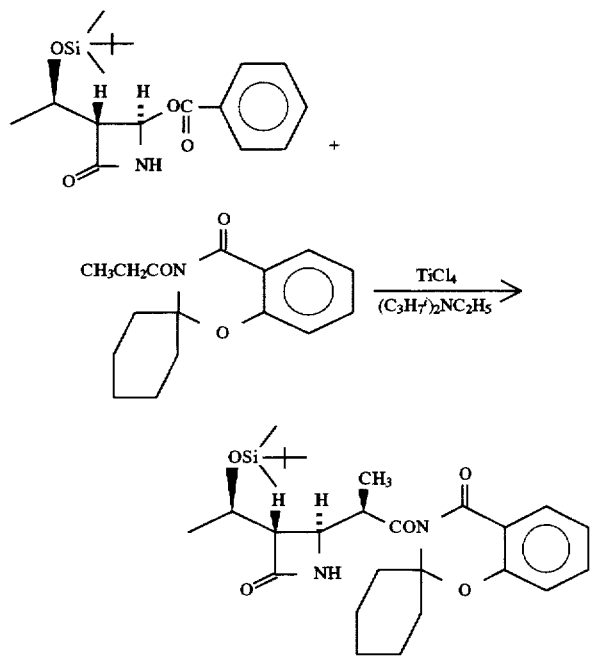

To a solution of 2,3-dihydro-2,2-pentamethylene-3-propionyl-4H-1,3-benzoxazin-4-one (4.15 g, 15.2 mmol) in methylene chloride (15 ml), titanium tetrachloride (2.99 g, 15.8 mmol) was added at 5° C. After stirring at the same temperature for 5 minutes, a solution of N,N-diisopropylethylamine (1.91 g, 14.8 mmol) in methylene chloride (10 ml) and a solution of (3R,4R)-4-benzoyloxy-3-[(R)-1-tert-butyldimethyl-silyloxyethyl]azetidin-2-one (3.81 g, 10.9 mmol) in methylene chloride (15 ml) were successively added thereto. Then the mixture thus obtained was heated to 30° C. and stirred for 2 hours. The mixture was cooled to 0° C. and poured into ice/water under stirring. Then the organic layer was separated, washed with water and analyzed by HPLC. The result showed that it contained 4.7 g of the β-methyl derivative (β-methyl derivative:α-methyl derivative=98.6:1.4).

Example 22

Production of β-methyl derivative (3-[(R)-2-[(3S,4R)-3-[(R)-1-tert-butyldimethylsilyloxyethyl]-2-oxoazetidin-4-yl) propionyl]-2,3-dihydro-2,2-pentamethylene-4H-1,3-benzoxazin-4-one):

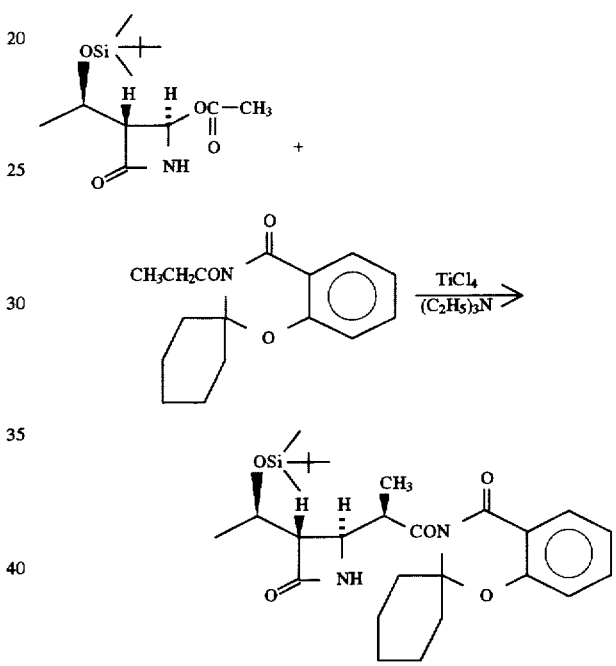

A solution of 2,3-dihydro-2,2-pentamethylene-3-propionyl-4H-1,3-benzoxazin-4-one (5.5 g, 20.1 mmol) in methylene chloride (55 ml) was cooled to 5° C. and a solution of titanium tetrachloride (3.8 g, 20 mmol) in methylene chloride (5 ml) was added thereto. After aging at 5° C. for 30 minutes, a solution of triethylamine (2.0 g, 20.1 mmol) in methylene chloride (5 ml) and a solution of (3R,4R)-4-acetoxy-3-[(R)-1-tert-butyldimethylsilyloxyethyl]azetidin-2-one (2.9 g, 10.0 mmol) in methylene chloride (10 ml) were successively added thereto at the same temperature. Then the mixture thus obtained was aged at 5° C. for 1 hour, heated to 20° C. and then aged again for 3 hours. The obtained mixture was added to 150 ml of water at 5° C. under stirring and aged at the same temperature for 30 minutes. Then the organic layer was separated and analyzed by HPLC. The result showed that it contained 4.2 g of the β-methyl derivative (β-methyl derivative:α-methyl derivative=98.6:1.4).

Example 23

Production of β-methyl derivative (3-[(R)-2-[(3S,4R)-3-[(R)-1-tert-butyldimethylsilyloxyethyl]-2-oxoazetidin-4-yl)

propionyl]-2,3-dihydro-2,2-dimethyl-4H-1,3-benzoxazin-4-one):

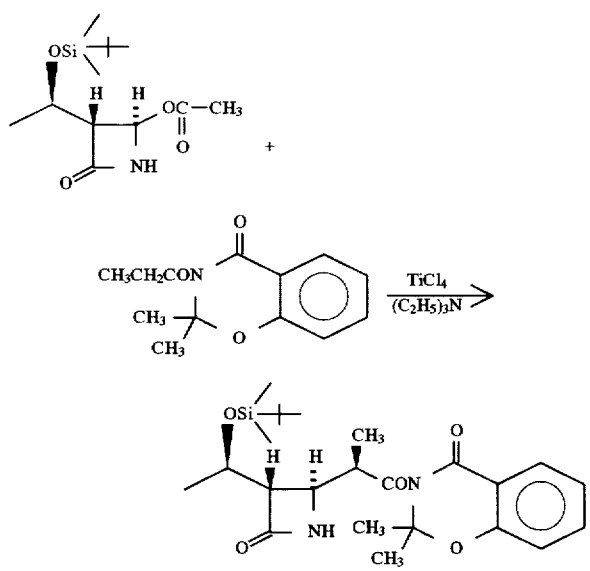

A solution of 2,3-dihydro-2,2-dimethyl-3-propionyl-4H-1,3-benzoxazin-4-one (4.5 g, 19.3 mmol) in methylene chloride (125 ml) was cooled to 5° C. and a solution of titanium tetrachloride (3.7 g, 19.3 mmol) in methylene chloride (5 ml) was added thereto. After aging at 5° C. for 30 minutes, a solution of triethylamine (2.0 g, 19.3 mmol) in methylene chloride (5 ml) and a solution of (3R,4R)-4-acetoxy-3-[(R)-1-tert-butyldimethylsilyloxyethyl] azetidin-2-one (2.8 g, 9.7 mmol) in methylene chloride (20 ml) were successively added thereto at the same temperature. Then the mixture thus obtained was aged at 5° C. for 1 hour, heated to 20° C. and then aged again for 3 hours. The obtained mixture was added to 300 ml of water at 5° C. under stirring and aged at the same temperature for 30 minutes. Then the organic layer was separated and analyzed by HPLC. The result showed that it contained 3.8 g of the β-methyl derivative (β-methyl derivative:α-methyl derivative=98.6:1.4).

[Referential Example 1]

Production of (R)-2-[(3S,4S)-3-[(R)-1-tert-butyldimethylsilyloxyethyl]-2-oxoazetidin-4-yl]propionic acid:

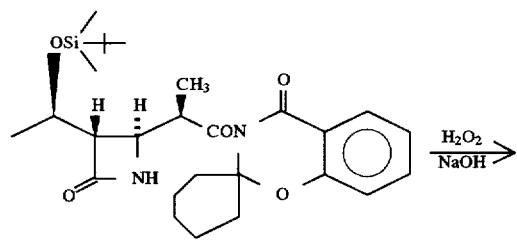

To a solution of 3-[(R)-2-[(3S,4R)-3-[(R)-1-tert-butyldimethylsilyloxyethyl]-2-oxoazetidin-4-yl]propionyl]-2,3-dihydro-2,2-pentamethylene-4H-1,3-benzoxazin-4-one (2.0 g, 4 mmol) in a solvent mixture of acetone/water (2:1, 15 ml), a 300% aqueous solution of hydrogen peroxide (1.5 g, 13.2 mmol) was added at room temperature. Then a 28% aqueous solution of sodium hydroxide (1.9 g, 13.2 mmol) was added dropwise into the mixture at the same temperature followed by aging for 2 hours. To the mixture thus obtained, 30 ml of water at 5° C. was added. Further, 3 ml of 35% hydrochloric acid was added at room temperature to thereby adjust the pH value of the mixture to 10.0. After washing with 50 ml of methylene chloride, 10 ml of 35% hydrochloric acid was added at the same temperature to thereby adjust the pH value of the mixture to 2.0. The crystals thus precipitated were collected by filtration and dried. Thus 0.9 g of (R)-2-[(3S,4S)-3-[(R)-1-tert-butyldimethylsilyloxyethyl]-2-oxoazetidin-4-yl ]propionic acid was obtained.

[Referential Example 2]

Production of (R)-2-[(3S,4S)-3-[(R)-1-tert-butyldimethylsilyloxyethyl]-2-oxoazetidin-4-yl]propionic acid:

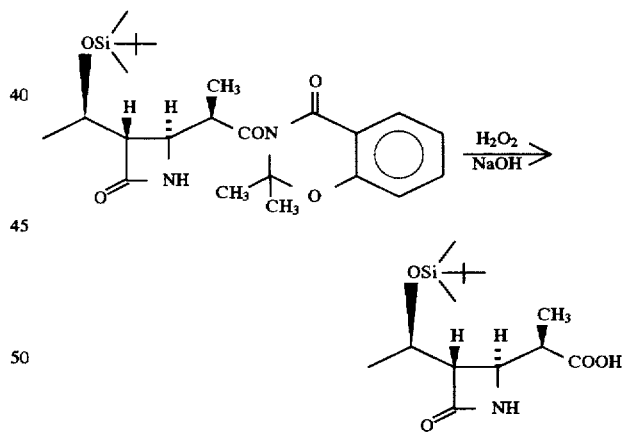

To a solution of 3-[(R)-2-[(3S,4R)-3-[(R)-1-tert-butyldimethylsilyloxyethyl]-2-oxoazetidin-4-yl]propionyl]-2,3-dihydro-2,2-dimethyl-4H-1,3-benzoxazin-4-one (7.0 g, 15 mmol) in a solvent mixture of methanol/water (2:1, 45 ml), a 30% aqueous solution of hydrogen peroxide (3.5 g, 30 mmol) was added at room temperature. Then a 28% aqueous solution of sodium hydroxide (2.4 g, 17 mmol) was added dropwise into it and the obtained mixture was stirred until the starting material disappeared in HPLC. After the completion of the reaction, 45 ml of cold water was added to the reaction mixture. After washing with 15 ml of methylene chloride, 35% hydrochloric acid was added to thereby adjust the pH value of the mixture to 3. The crystals thus precipitated were collected by filtration, washed with water and dried. Thus 4.3 g of (R)-2-[(3S,4S)-3-[(R)-1-tert-butyldimethylsilyloxyethyl]-2-oxoazetidin-4-yl]propionic acid was obtained.

The production process according to the present invention with the use of the compound represented by the general formula [V], which is inexpensive and easy to handle, is an excellent method from an industrial viewpoint.

When $R^2$ is an alkyl group such as a methyl group, the β-compound, which is important as an intermediate in the synthesis of carbapenem compounds, can be selectively obtained by regulating the molar ratio or selecting an appropriate auxiliary group.

What is claimed is:

1. A process for the production of a 4-substituted azetidinone derivative which comprises reacting an azetidinone derivative represented by the following formula:

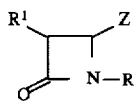

wherein R represents a hydrogen atom or a protecting group for N which can easily be eliminated, $R^1$ represents an alkyl group which may be a substituent having an unprotected or protected hydroxyl group; and Z represents a leaving group; with an imide compound represented by the following formulae:

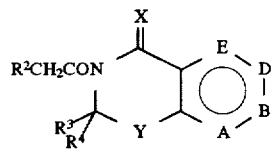

or

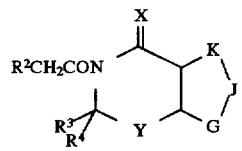

wherein $R^2$ represents a hydrogen atom or an alkyl group, $R^3$ and $R^4$ each represent a hydrogen atom, an alkyl group, an alkenyl group, an alkynyl group, a phenyl group, a cycloalkyl group, or a naphthyl group, or $R^3$ and $R^4$, together with the carbon atom to which they are bonded, form a ring system selected from the group consisting of the following formulae:

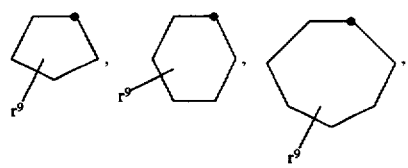

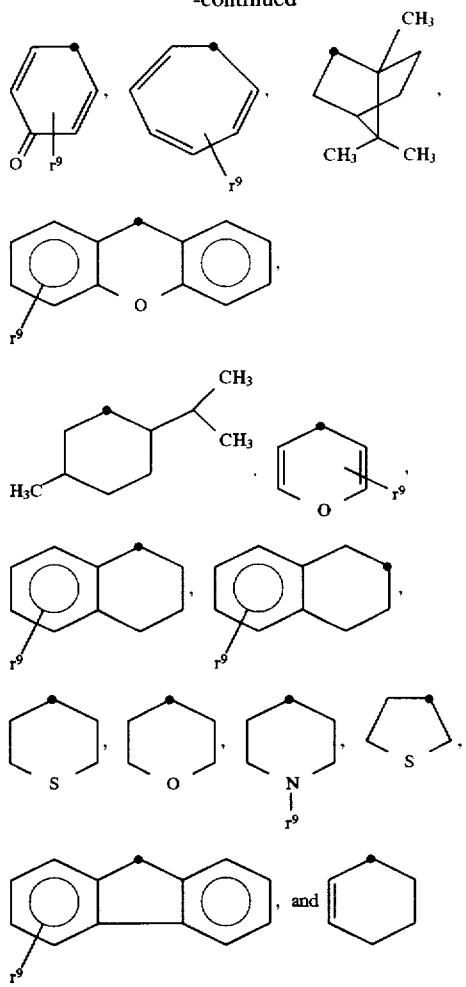

in which ● represents the carbon atom to which [$R^4$] $R^3$ and $R^4$ are bonded and $r^9$ represents a hydrogen atom, an alkyl group having 1 to 10 carbon atoms, a lower alkoxy group having 1 to 4 carbon atoms, a phenoxy group, a lower alkylthio group having 1 to 3 carbon atoms, a phenylthio group, a nitro group, a cyano group, an amino group substituted by a lower alkyl group having 1 to 4 carbon atoms, or an N-methylanilino group; X and Y each represent an oxygen atom, a sulfur atom or N-$r^1$, wherein $r^1$ represents a hydrogen atom or a lower alkyl group; A, B, D and E each represent a nitrogen atom or C-$r^2$, wherein $r^2$ represents a hydrogen atom, a halogen atom, a lower alkyl group or a lower alkoxy group, provided that at least two of A, B, D and E are C-$r^2$; and a five-membered ring involving G, J and K has two carbon/carbon double bonds therein and one of G, J and K represents an oxygen atom, a sulfur atom or N-$r^1$ while the remaining two represent C-$r^2$; wherein $r^1$ and $r^2$ are as defined above; in the presence of a compound represented by the following formula:

$$M(Hal)_n(R^5) \quad (V)$$

wherein M represents a metal atom; Hal represents a halogen atom; $R^5$ represents a lower alkyl group, a lower alkoxy group, a phenoxy group, a substituted phenoxy group or a cyclopentadienyl group; and n and m are each 0, 1, 2, 3, 4 or 5, provided that n+m stands for the valence of M; and a base to thereby give a 4-substituted azetidinone derivative represented by the following formula:

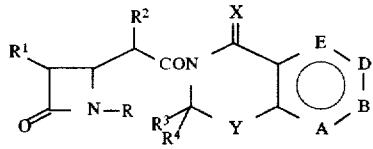
(II-1)

or

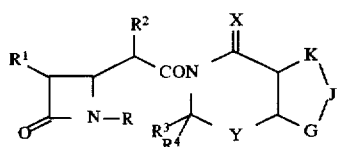
(II-2)

wherein R, R¹, R², R³, R⁴, X, Y, A, B, D, E, G, J, and K are as defined above.

2. A process as claimed in claim 1 wherein M is Ti, Zr or Sn and m+n is 4.

3. A process as claimed in claim 1 wherein M is Al and m+n is 3.

4. A process as claimed in claim 1 wherein $M(Hal)_n(R^5)_m$ is $TiCl_4$.

5. A process as claimed in claim 1 wherein $M(Hal)_n(R^5)_m$ is $ZrCl_4$.

6. A process as claimed in claim 1 wherein $M(Hal)_n(R^5)_m$ is $AlCl_3$.

7. A process as claimed in claim 1 wherein $M(Hal)_n(R^5)_m$ is $AlCl(C_2H_5)_2$.

8. A process as claimed in claim 1 wherein the compound of formula (II-1) or (II-2) is hydrolyzed to form

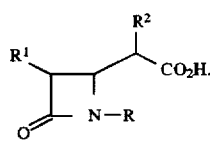
(I)

9. A process as claimed in claim 1 wherein the 4-substituted azetidinone formed having formula (II-1) or (II-2) is

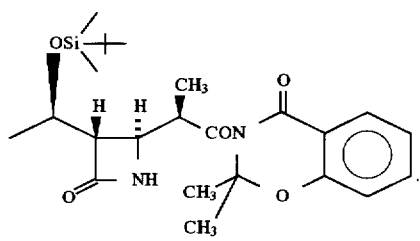

10. A process as claimed in claim 1 wherein the 4-substituted azetidinone formed having formula (II-1) or (II-2) is

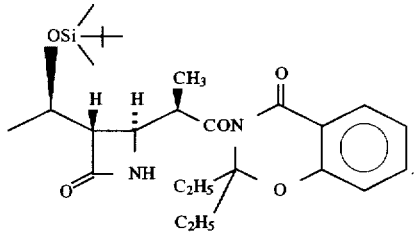

11. A process as claimed in claim 1 wherein the 4-substituted azetidinone formed having formula (II-1) or (II-2) is

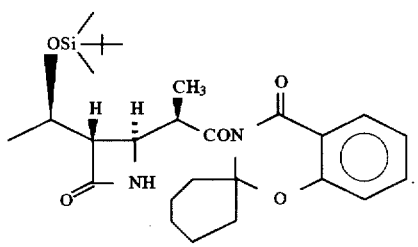

12. A process as claimed in claim 1 wherein the 4-substituted azetidinone formed having formula (II-1) or (II-2) is

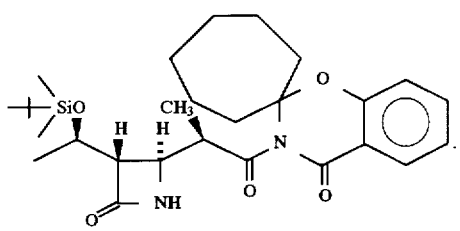

13. A process as claimed in claim 1 wherein the 4-substituted azetidinone formed having formula (II-1) or (II-2) is

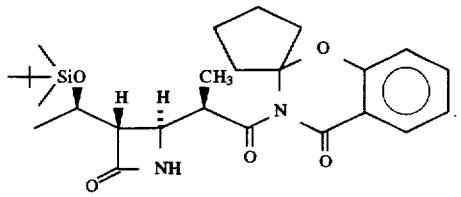

14. A process as claimed in claim 1 wherein the azetidinone derivative of formula (III) is

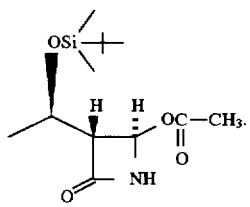

15. A process as claimed in claim 1 wherein the azetidinone derivative of formula (III) is

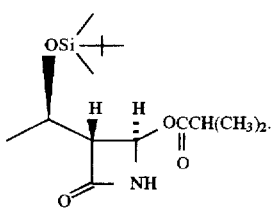

16. A process as claimed in claim 1 wherein the azetidinone derivative of formula (III) is

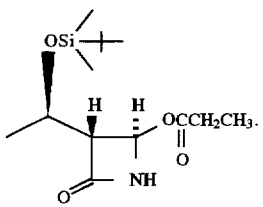

17. A process as claimed in claim 1 wherein the azetidinone derivative of formula (III) is

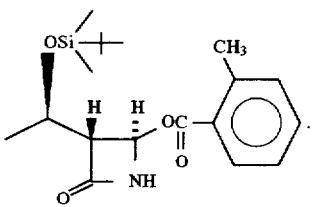

18. A process as claimed in claim 1 wherein the azetidinone derivative of formula (III) is

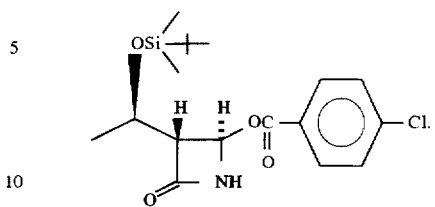

19. A process as claimed in claim 1 wherein the azetidinone derivative of formula (III) is

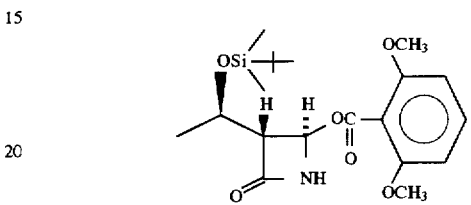

20. A process as claimed in claim 1 wherein the azetidinone derivative of formula (III) is

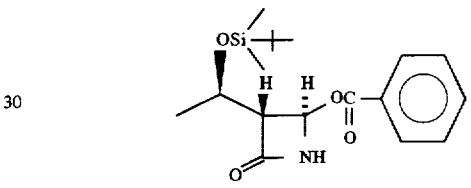

* * * * *